United States Patent [19]

Bundy

[11] 4,067,991

[45] Jan. 10, 1978

[54] PHARMACEUTICAL COMPOSITIONS AND METHOD OF USE FOR PROSTAGLANDIN 1,11- AND 1,15-LACTONES

[75] Inventor: Gordon L. Bundy, Portage, Mich.

[73] Assignee: The Upjohn Company, Kalamazoo, Mich.

[21] Appl. No.: 692,439

[22] Filed: June 3, 1976

Related U.S. Application Data

[63] Continuation of Ser. No. 589,724, June 23, 1975, abandoned.

[51] Int. Cl.$^2$ .......................................... A61K 31/365
[52] U.S. Cl. .................................................. 424/279
[58] Field of Search ........................................ 424/279

[56] References Cited

U.S. PATENT DOCUMENTS 3,872,107   3/1975   Crabbe ............................... 424/279

*Primary Examiner*—Sam Rosen
*Attorney, Agent, or Firm*—Robert A. Armitage; Earl C. Spaeth

[57] ABSTRACT

There are described pharmaceutical compositions comprising a lactone which is the 1,9-lactone, the 1,11-lactone, or the 1,15-lactone of a prostaglandin or prostaglandin analog in combination with a pharmaceutical carrier and formulated to deliver said prostaglandin or prostaglandin analog to an esterase-containing tissue area of a mammal. Also disclosed are methods for administering said compositions to a mammal.

38 Claims, No Drawings

PHARMACEUTICAL COMPOSITIONS AND METHOD OF USE FOR PROSTAGLANDIN 1,11- AND 1,15-LACTONES

CROSS REFERENCE TO RELATED APPLICATIONS

This application is a continuation of Ser. No. 589,724, filed June 23, 1975, now abandoned.

DESCRIPTION OF THE INVENTION

This invention relates to novel pharmaceutical compositions of matter and to methods for using them. More specifically, this invention is concerned with pharmaceutical compositions intended for use in the administration of prostaglandins and prostaglandin analogs to mammals, including humans and domestic animals, especially swine and animals of the genus Bos, and small animals, especially cats, dogs and laboratory animals. This invention is also specifically concerned with methods for administration of said compositions to said mammals.

Prostaglandins are related in structure to the substance known as prostanoic acid which has the formula and atom numbering:

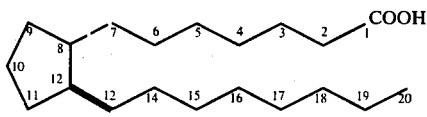   I

Numerous prostaglandins are known in the art. For example, the compound known as prostaglandin $E_2$ ($PGE_2$) has the formula:

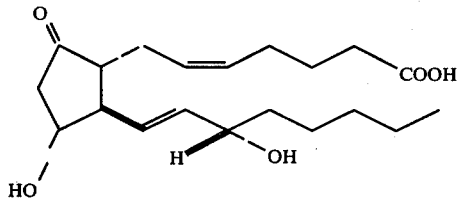   II and prostaglandin $F_{2\alpha}$ ($PGF_{2\alpha}$) has the formula:

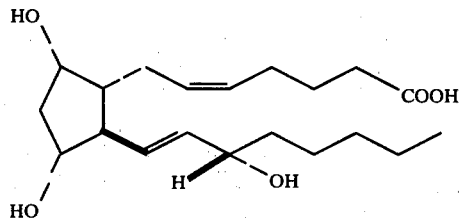

Other prostaglandins of the E-type and F-type are also known in the art. For example, $PGE_1$ lacks the 5,6-double bond of $PGE_2$, and $PGE_3$ has a cis-17,18-double bond but otherwise has the same structure as $PGE_2$. $PGF_{1\alpha}$ and $PGF_{3\alpha}$ differ from $PGF_{2\alpha}$ in the same manner. $PGF_{2\beta}$ has the same structure as $PGF_{2\alpha}$ except the 9—OH is attached in $\beta$-configuration. PGA-type prostaglandins all have the ring:

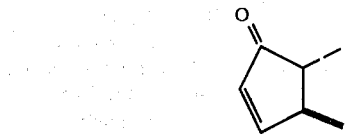

and PGB-type prostaglandins all have the ring:

but otherwise these are the same in structure as the PGE-type and PGF-type prostaglandins. A very large number of prostaglandin analogs are also known in the art. These differ from the prostaglandins in one or more of various structural features. For example, one or more of the stereochemical features of the prostaglandin structure is altered, one or more of a large variety of substituents at one or more of the various positions on the prostaglandin structure are present, the length of either or both chains is different than in the prostaglandins, one of the oxygen atoms attached to the ring is absent, or any of a large variety of different structural features in introduced into one or both chains, for example, an oxa or a thia atom or a phenylene moiety in place of one or more of the methylene groups in a chain.

As is apparent from reading the very extensive prior art relating to prostaglandins and prostaglandin analogs, including U.S. and foreign patents, published foreign patent applications, and non-patent published literature, prostaglandins and prostaglandin analogs are useful for a large variety of medical and pharmacological purposes in treating mammals, including humans, useful domestic animals, and small animals, including pets, e.g., cats and dogs, and laboratory animals. One very serious problem in using prostaglandins and prostaglandin analogs in the treatment of mammals is that most prostaglandins and prostaglandin analogs are rapidly metabolized by various mammalian enzymatic processes. Thus, these compounds frequently have a relatively short duration of action. Another problem concerning use of the known prostaglandins and prostaglandin analogs is that many of these are oils or low melting solids and for that reason are difficult to handle and formulate into pharmaceutically useful compositions. Moreover, many of these known compounds are of relatively low chemical stability and are subject to relatively rapid decomposition and autoxidation, compared with the majority of other pharmaceutical compositions used in treating mammals.

I have now made the surprising and unexpected discovery that 1,9-lactones, 1,11-lactones, and 1,15-lactones of each of the known prostaglandins and prostaglandin analogs wherein the 1-position (see formula 1 above) is carboxy and there is a hydroxy at C-9, C-11, or C-15, respectively, can be prepared as described hereinbelow, and that each of these lactones is a preferred form of each of those known prostaglandins and prostaglandin analogs for administration in appropriate pharmaceutical dosage form to mammals by the routes of administration stated in the art and for medical and pharmacological purposes stated in the art for each such prostaglandin and prostaglandin analog. One reason for this preference is that these lactones, 1,9-, 1,11-, and 1,15-, are generally of greater chemical stability than the corresponding prostaglandin or prostaglandin analog, and are more often crystalline than the corresponding prostaglandin or prostaglandin analog. When the prostaglandin or prostaglandin analog is itself crystalline, the lactone form is generally of higher melting point and easier to purify. Moreover, these lactones are generally more readily and easily handled and transformed to useful pharmaceutical dosage forms than the corresponding prostaglandins or prostaglandin analogs.

In addition to the above-described advantages of 1,9-, 1,11-, 1,15-lactones, there are even more substantial advantages with respect to the results obtained when a lactone is administered in place of the corresponding prostaglandin or prostaglandin analog. Some of these advantages are as follows:

1. Improved IV tolerance.

The known prostaglandins and prostaglandin analogs are frequently administered by intravenous infusion. The concentration reached locally in the vein through which these are infused is substantially higher than the concentration needed elsewhere to produce the intended effect. Because the administered compounds are frequently very potent, rapidly acting, and of relatively short half-life, the pharmacologic effect of the administered drug of the infusion vein may limit the rate of infusion and the locally tolerated concentration. Although rare, adverse local reactions have been reported with $PGF_{2\alpha}$, $PGE_1$ and $PGE_2$ when the infusion rate was excessive. The lactones of this invention are pro-drugs, and, while not biologically inert, they nonetheless exhibit very substantially reduced direct and immediate effects and thus may be administered by the intravenous route with much improved local tolerance.

2. More consistent release from 1M injection sites.

The known prostaglandins and prostaglandin analogs commonly affect vascular smooth muscle, causing constriction or dilatation, depending on their structure. Thus $PGE_1$ and $PGA_2$ are often vasodilator while $PGF_{2\alpha}$ and $PGB_2$ are often vasoconstrictor. Some prostaglandins are biphasic causing first dilatation and later constriction, and v.v. Moreover the vascular effects are often species-dependent and sometimes even tissue dependent. When administered by the intramuscular route, often to obtain prolonged duration of action, drugs in general are released at a rate which is partially dependent on vascular flow around the site of administration. Indeed, to delay the release of drugs and to prolong their activity, vasoconstrictors such as epinephrine have occasionally been added to the IM formulation. it is immediately evident that the biological effects of prostaglandins which are given intramuscularly and which exhibit vascular smooth muscle activity are to a degree influenced by the local vascular effects they produce. Moreover, the study of the biological effects of prostaglandins in animals, when given by the IM route, is to a degree influenced by the local vascular effects at their injection sites. Since species differences are well recogniaed for these prostaglandin effects, the translation of laboratory animal responses by the IM route to expected responses in m man is to that extent less certain. Since the lactones of this invention lack marked local and immediate effects, their systemic effects are less influenced by variable local vascular effects after IM administration and they thus constitute a particularly good delivery system for the prostaglandins.

3. More stable blood levels.

When known prostaglandins and prostaglandin analogs are administered to man or to domestic animals for an intended biological effect, whether IV, SQ, IM, or oral, the active material appears rapidly in the blood and, commonly disappears rapidly as a result of metabolism, particularly by enzymatic dehydrogenation of the 15-hydroxyl group and enzymtic $\beta$-oxidation of the acidic chain. Metabolites of the prostaglandins appear rapidly in the urine. As a result of the rapid entry and departure of prostaglandins, blood levels generally peak at levels much higher than needed and may thus produce undesired effects. These effects can be minimized by giving the prostaglandins in the form of their 1,9-, 1,11-, or 1,15-lactones which are converted enzymatically in vivo into the parent prostaglandin substantially decreasing the excessive peaks of active drug and slowing the metabolic inactivation of the administered pro-drug to give a more even biological response.

4. Improved selectivity of action and therapeutic ratio.

Because known prostaglandins and prostaglandin analogs affect directly a variety of tissues, including gastrointestinal smooth muscle, when they are used to produce a principal desired effect, it is common to produce concommitantly a spectrum of associated and often undesired effects. Notable among these are nausea and vomiting, diarrhea, and occasionally increases in pulmonary artery pressure. The lactones of this invention exhibit these undesired effects, if at all, to a markedly diminished degree.

The 1,9-lactones, the 1,11-lactones, and the 1,15-lactones of the known prostaglandins and prostaglandin analogs are hydrolyzed enzymatically in mammalian tissues which contain significant amounts of ester hydrolytic enzymes. These enzymes are also known as esterases. The hydrolysis product is the prostaglandin or prostaglandin analog corresponding to the lactone. After this enzymatic hydrolysis, of course, said prostaglandin or prostaglandin analog is then available at the hydrolysis site or at wherever the mammalian body transport mechanisms take the prostaglandin or prostaglandin analog.

Many mammalian tissues contain relatively low levels of esterases. Therefore, when these lactones are in contact with such tissues, the 1,9-, 1,11-, and 1,15-lactone rings remain largely intact, and the generally undesirable effects of the prostaglandins and prostaglandin analogs are not observed. But when the mammalian transport mechanisms, for example, the blood stream, bring these lactones into contact with tissues relatively rich in esterases, there the lactone rings are opened, and there the resulting prostaglandins and prostaglandin analogs are able to cause the expected and desired medical and pharmacological effects.

Thus, this invention is pharmaceutical compositions comprising a lactone which is the 1,9-lactone, the 1,11-lactone, or the 1,15-lactone of a prostaglandin in combination with a pharmaceutical carrier and formulated to deliver said prostaglandin or prostaglandin analog to an esterase-containing tissue area of a mammal.

Those skilled in the art know which mammalian tissues are rich in esterases and which are poor in esterases, and thus it will be apparent to those skilled in the art how to use the lactones of this invention to administer prostaglandins and prostaglandin analogs to cause desired medical and pharmacological effects in mammals. Tissues and organs particularly responsive to prostaglandins and prostaglandin analogs administered in the form of 1,9-, 1,11-, and 1,15-lactones include ovary, corus luteum, graafien follicle, uterus, leukocyte, brain, lung, and serosal side of the gastrointestinal tract. Tissues and organs less sensitive include vascular smooth muscle, mucosal side of gastrointestinal tract, erythrocytes, and trachea.

There is still another advantage of using 1,9-lactones, 1,11-lactones, and 1,15-lactones of prostaglandins and prostaglandin analogs as pro-drugs capable of generating the corresponding prostaglandin or prostaglandin analog. Prostaglandins and a majority of the known prostaglandin analogs are relatively rapidly metabolized by oxidation of the 15-hydroxyl group, by successive $\beta$-oxidation of the acidic chain, and to a lesser degree by terminal oxidation of the alkyl chain. These metabolic transformations appear to be accompanied by substantial and rapid losses of biological activity. The 1,9- and 1,11-lactones are protected from $\beta$-oxidation and are substantially protected from oxidation at C-15 while the 1,15-lactones are protected both from $\beta$-oxidation and from oxidation at C-15. Protection from these common metabolic pathways lasts until the lactones are enzymatically opened to afford the corresponding parent prostaglandins. As pro-drugs, the lactones are non-acidic and more lipophylic. Whereas PGE$_2$ and PGF$_{2\alpha}$ are over 90% metabolized in one pass through the lung, the 1,9-, 1,11-, and 1,15-lactones have far longer half-lives and may be taken up in fat and other tissues and released slowly therefrom to provide a more prolonged or sustained effect. Thus, the lactones of this invention comprise an effective drug delivery system, providing a relatively sustained and selective activity and an improved therapeutic ratio. They may be used in place of their corresponding parent prostaglandins to produce those useful effects characteristic of said parents with a decrease in undesired local and gastrointestinal side effects and an increased selectivity of action and duration of activity.

General processes are described and exemplified hereinbelow for the preparation of 1,9-lactones, 1,11-lactones, and 1,15-lactones. Any of the known prostaglandins and prostaglandin analogs are transformed to 1,9-lactones, 1,11-lactones, and 1,15-lactones as long as said prostaglandins and prostaglandin analogs all contain a free carboxy group as position 1 (see formula I above), and contain a free hydroxy at C-9 for the 1,9-lactones, at C-11 for the 1,11-lactones, and at C-15 for the 1,15-lactones. Among the known prostaglandins which are used to make 1,15-lactones useful within the scope of this invention are PGE$_1$, PGE$_2$, PGE$_3$, dihydro-PGE$_1$, PGF$_{1\alpha}$, PGF$_{2\alpha}$, PGF$_{3\alpha}$, dihydro-PGF$_{1\alpha}$, PGF$_{1\beta}$, PGF$_{2\beta}$PGF$_{3\beta}$, dihydro-PGF$_{1\beta}$, PGA$_1$, PGA$_2$, PGA$_3$, 13,14-dihydro-PGA$_1$, PGB$_1$, PGB$_2$, PGB$_3$, and 13,14-dihydro-PGB$_1$. Of these known prostaglandins, the PGE-type, the PGF$_{60}$-type, and the PGF$\beta$-type compounds are used to make 1,11-lactones useful within the scope of this invention. Also, of these known prostaglandins, the PGF$_\alpha$-type and PGF$_\beta$-type compounds are used to make 1,9-lactones useful within the scope of this invention.

With regard to analogs, PGF$_\alpha$-type and PGF$_\beta$-type analogs with a hydroxy at C-15 are useful to make 1,9-lactones, 1,11-lactones, and 1,15-lactones. PGE-type analogs with a hydroxy at C-15 are useful to make 1,11-lactones and 1,15-lactones. PGA-type analogs and PGB-type analogs are useful only to make 1,15-lactones.

PGD-type analogs are known compounds which are like PGE-type compounds, differing therefrom in that the cyclopentane ring contains alpha hydroxy or beta hydroxy at C-9 and oxo at C-11 rather than the reverse as in PGF-type compounds. PGD-type compounds which contain a C-15 hydroxy are used to make C-9 lactones and C-15 lactones useful within the scope of this invention.

9-Deoxy-PGF$_\alpha$-type analogs, 9-deoxy-PGF$_\beta$-type analogs, and corresponding 11-deoxy-PGF-type analogs are known compounds which differ from PGF$_\alpha$-type and PGF$_\beta$-type compounds in that the 9-deoxy compounds do not have a C-9 hydroxy, while the 11-deoxy compounds do not have a C-11 hydroxy. The 9-deoxy-PGF-type compounds which contain a C-15 hydroxy are used to make C-11 lactones and C-15 lactones, while the 11-deoxy-PGF-type compounds which contain a C-15 hydroxy are used to make C-9 lactones and C-15 lactones, all of which lactones are useful within the scope of this invention.

Also especially preferred embodiments of this invention are pharmaceutical compositions containing lactones and methods of using them involving 1,9-lactones, 1,11-lactones, and 1,15-lactones corresponding to prostaglandin analogs which have as analog structural features one or more of the following: one or two methyl substituents at C-16, a methyl substituent at C-15, an oxa in place of the C-3 or C-5 methylene, one or 2 fluoro at C-2, a phenyl or phenoxy moiety unsubstituted or substituted with methyl, chloro, bromo, or trifluoromethyl, especially at the meta or para position, in place of part of the methyl-terminated chain of prostaglandins, a cis-13,14 double bond or a 13,14-acetylenic triple bond in place of the usual trans-13,14 double bond of prostaglandins, and the carboxy-terminated chain and the methyl-terminated chains attached to the cyclopentane ring in beta and alpha configurations, respectively, rather than in alpha and beta configurations, respectively, as in prostaglandins. Prostaglandin analogs with such features are known in the art, and the 1,9-, 1,11-, and 1,15-lactones of those are prepared as described generally below.

There are many other prostaglandin analogs known in the art. See, for example, the following U.S. patents, and the following published German Offenlegungsschrifts, Belgian patents, and Dutch patent applications:

| | |
|---|---|
| U.S. 3,432,541 | U.S. 3,813,433 |
| U.S. 3,455,992 | U.S. 3,833,640 |
| U.S. 3,579,425 | U.S. 3,835,179 |
| U.S. 3,639,463 | U.S. 3,835,180 |
| U.S. 3,678,092 | U.S. 3,836,578 |
| U.S. 3,696,144 | U.S. 3,840,573 |
| U.S. 3,707,548 | U.S. 3,843,713 |
| U.S. 3,725,454 | U.S. 3,847,966 |
| U.S. 3,728,382 | U.S. 3,849,474 |
| U.S. 3,751,463 | U.S. 3,849,487 |
| U.S. 3,755,426 | U.S. 3,852,316 |
| U.S. 3,759,978 | U.S. 3,862,984 |
| U.S. 3,767,695 | U.S. 3,864,387 |
| U.S. 3,767,813 | U.S. 3,867,377 |
| U.S. 3,770,776 | U.S. 3,867,423 |
| U.S. 3,773,795 | U.S. 3,868,413 |
| U.S. 3,775,462 | U.S. 3,870,710 |
| U.S. 3,776,940 | U.S. 3,870,711 |
| U.S. 3,781,325 | U.S. 3,872,107 |
| U.S. 3,787,448 | U.S. 3,873,607 |
| U.S. 3,801,623 | U.S. 3,878,239 |
| U.S. 3,808,258 | U.S. 3,879,438 |
| | U.S. 3,883,659 |

-continued

| | |
|---|---|
| Belgium 763,999 | Belgium 792,803 |
| Belgium 764,000 | Belgium 800,953 |
| Belgium 766,521 | Belgium 802,385 |
| Belgium 767,704 | Belgium 802,386 |
| Belgium 772,836 | Belgium 805,111 |
| Belgium 779,898 | Belgium 806,995 |
| Belgium 782,822 | Belgium 811,665 |
| Belgium 788,415 | Belgium 813,547 |
| Belgium 789,407 | Belgium 814,028 |
| Dutch 7,206,361 | Dutch 7,305,304 |
| Dutch 7,208,955 | Dutch 7,307,740 |
| Dutch 7,209,817 | Dutch 7,309,792 |
| Dutch 7,217,607 | Dutch 7,310,277 |
| Dutch 7,301,094 | Dutch 7,311,403 |
| Dutch 7,305,222 | Dutch 7,313,322 |
| | Dutch 7,401,448 |
| German 1,937,675 | German 2,320,368 |
| German 2,011,969 | German 2,320,552 |
| German 2,036,471 | German 2,322,673 |
| German 2,137,811 | German 2,323,127 |
| German 2,150,361 | German 2,332,400 |
| German 2,154,309 | German 2,345,695 |
| German 2,165,184 | German 2,353,788 |
| German 2,209,990 | German 2,355,324 |
| German 2,213,907 | German 2,357,781 |
| German 2,217,044 | German 2,360,893 |
| German 2,262,608 | German 2,364,706 |
| German 2,263,393 | German 2,404,654 |
| German 2,317,019 | |

Each of the above mentioned Belgian patents is available as a printed publication through the Central Patents Index of Derwent Publications, Ltd.

Each of the prostaglandin analogs described in each of the above mentioned U.S. and Belgium patents and in each of the above mentioned German Offenlegungsschrifts and Dutch patent applications which contain carboxy at position 1, and hydroxy at C-9, C-11, and/or C-15 is transformed to the corresponding 1,9-lactone, 1,11-lactone, and/or 1,15-lactone, using the chemical processes generally described and specifically exemplified below. Each of said 1,9-, 1,11-, and 1,15-lactones is used according to this invention in a pharmaceutical composition as a means of administering the corresponding prostaglandin analog to esterase-containing mammalian tissue areas to accomplish the medical or pharmacological purposes set forth in the particular patent or patent application describing said analog or to accomplish other medical or pharmacological purposes described for that analog in other prior art. Especially preferred 1,9-lactones, 1,11-lactones, and 1,15-lactones of these various prostaglandin analogs for use according to this invention and as described herein are the lactones of the various prostaglandin analogs indicated in each of the above mentioned patents and patent applications as preferred and especially preferred for use for particular medical or pharmacological purposes described therein.

In using the various 1,9-, 1,11-, and 1,15-lactones described hereinabove and exemplified hereinbelow, the lactone is used in combination with the usual pharmaceutical carriers which adapt the lactone for administration to the mammal by the chosen route of administration. For example, if the route of administration is to be by intravenous injection or infusion, sterile aqueous isotonic solutions of the lactone are used. The actual formulation of pharmaceutical compositions containing 1,9-lactones, 1,11-lactones, and 1,15-lactones of prostaglandins and prostaglandin analogs according to this invention is, however, within the skill of the art. With regard to administration of these lactone-containing pharmaceutical compositions, the routes of administration are generally the same as used for the parent prostaglandins and prostaglandin analogs. With regard to dosages, any particular molecular amount of a 1,9-, 1,11-, or 1,15-lactone should give rise in the presences of mammalian esterases to an equal molecular amount of the parent prostaglandin or prostaglandin analog, but it is appropriate for one skilled in the art of administering prostaglandins to start mammalian treatment with substantially less than this amount, advantageously in a dosage range about one-tenth of that normally used and recommended for the parent prostaglandin or prostaglandin analog. The reason for this is the substantially slower rate of metabolism of these lactones compared with the rate of metabolism of the parent prostaglandin or prostaglandin analog. Thus, a larger proportion of the prostaglandin or prostaglandin analog (in the form of the lactone) can be expected to reach the esterase-rich tissue site where the prostaglandin or prostaglandin analog is expected to cause the desired medical or pharmacological effects. Since there are known to be variations among animals species and even among individuals within a group of animals or humans with regard to distribution and levels of esteraces in the various mammalian tissues, the most effective dose of a lactone for a particular desired medical or pharmacological result is best determined by starting at the above recommended low dose of lactone and gradually raising the dose level until the desired result is attained.

Another advantage in using 1,9-, 1,11- and 1,15-lactones in place of many of the known prostaglandins and prostaglandin analogs is that larger doses of the prostaglandin or prostaglandin analog can be administered in the form of the lactone than in the form of the parent prostaglandin. Administration of many prostaglandins and prostaglandin analogs to mammals, including humans, for particular medical or pharmacological purposes also results in undesirable side effects. It frequently happens that a larger dose of the prostaglandin or prostaglandin analog would be desired for medical or pharmacological purposes, but intolerable side effects would result from administration of that larger dose. These 1,9-, 1,11-, and 1,15-lactones usually cause substantially less and fewer side effects than the corresponding prostaglandins or prostaglandin analogs and for that reason are preferred dosage forms of the latter, especially when otherwise intolerably high doses of the prostaglandin or prostaglandin analog are desired.

The novel 1,9-lactones, 1,11-lactones, and 1,15-lactones of known biologically active prostaglandins and prostaglandin analogs, subject of this invention, are prepared from known prostaglandins and prostaglandin analogs which are carboxylic acids at $C_1$ and which possess additionally a 9-hydroxy-, 11-hydroxy-, and 15-hydroxy-group, respectively. The compounds of this invention are thus limited to those prostaglandins exhibiting useful biological activity, particularly prostaglandin-like biological activity. Accordingly the acidic side chain ordinarily attached to C-8 of prostanoic acid is, exclusive of any substituents it may contain, at least 5-atoms in length, including the terminal carboxy group, and is preferbly 6-9 atoms in length, thus including the usual 7-carbon chain and the 9-carbon chain present in prostaglandins and in 2a,2b-dibromo prostaglandins, respectively. As will be evidenced to one skilled in the art, chain length determines the size of the derived lactones and the size of the lactones determines the inherent strain, and difficulty of synthesis. In limiting the chain ordinarily attached to C-8 of prostanoic acid to 5-atoms or more, it has been taken into account not only biological activity but the inherent strain of the derived lactones. Clearly, however, these lactones which can not be made due to excessive bond distortion are excluded from the lactones of this invention.

The size of the 1,15-lactone ring of prostaglandins is 13 and is at least 11 for the 1,15-lactone of this invention.

The size of the 1,11-lactone ring of prostaglandins is 11 and is at least 9 for the 1,11-lactones of this invention, and at least 10 if the acid chain contains a trans double bond or an acetylene function.

In these natural prostaglandins, the groups attached at C-8 and at C-11 (when OH) are cis. In some prostaglandin analogs they are trans. When the stereochemistry is trans, the lactone ring size must be at least 11 and when a trans double-bond or allene function is included, must be at least 12.

The size of the 1,9-lactone ring of natural prostaglandins (e.g. $PGF_{2\alpha}$) is 10 and is at least 8 for the lactones of this invention and must be at least 9 if the acid obtained contains a trans double-bond, an acetylene function or an allene.

In the natrual prostaglandins the groups attached at C-8 and at C-9 (when OH) are cis. In the prostaglandin analogs they may be trans. When the stereochemistry is trans, the lactone ring size must be at least 10 if the acid chain contains an acetylene function.

As will be particularly evident to those skilled in the art, the preparation of a 1,9-, 1,11-, or 1,15-lactone will be relatively uncomplicated when the 9-, 11-, or 15-hydroxy group is the only free hydroxy group with which the carboxy function can lactonize. Thus, when more than one hydroxy group is present, as for example in $PGF_{2\alpha}$, those hydroxyl groups not required for lactone function are optionally derivatized prior to lactonization to require formation of the desired lactone. Selective methods for selective derivatization of all but one hydroxy of a prostaglandin or prostaglandin analog which contains two or more hydroxys are known in the art. Suitable derivatives are the 9,11-cyclic phenyl- or butyl-boronates of $9\alpha,11\alpha$- or $9\beta,11\beta$-dihydroxylated prostaglandins and prostaglandin analogs, acylates such as acetate, silyl ethers such as trimethylsilyl-, t-butyl-dimethylsilyl-, and triphenylsilyl and the like. Such functional derivatives are known in the prostaglandin art and are used with stereoselectivity or where stereoselectivity is not achievable, with careful purification of the mixtures produced, to obtain the desired functionally protected prostaglandins and prostaglandin analogs as exemplified further in the examples. Optionally, if desired, one or more hydroxy groups are protected by oxidation to a ketone before or after lactonization. After lactonization, the ketone is reduced again to produce a free hydroxy group of the same configuration or of opposite configuration to that originally present.

However, it is not essential in all cases to protect hydroxy groups which may be present but are not desired to participate in the lactone formation. Lactone formation occurs at different relative rates with different hydroxy groups depending on the stereochemistry, steric bulk in the vicinity of the hydroxy group, and ring size. Moreover it is possible to separate 1,9-, 1,11-, and 1,15-lactones as exemplified below for $PGF_{2\alpha}$ 1,9-, 1,11-, and 1,15-lactones. Thus 15-methyl-15-hydroxy- and 16,16-dimethyl-15-hydroxy prostaglandin analogs are sterically hindered in the vicinity of c-15 and lactone function at 15 will not compete with lctone function with a 9- or 11-hydroxy group. As a corollary, in order to make a lactone with a hindered hydroxy group such as 15-methyl-15-hydroxy- or 16,16-dimethyl-15-hydroxy-, it is essential that other hydroxy groups which may be present be protected. It is also necessary to extend the duration of the reaction until analysis of the reaction mixture indicates that some desired product is formed.

Prostaglandins known in the art as their lower alkyl (e.g. methyl, ethyl) ester but not as their free acid may be converted to the free acid for use in lactone function by chemical hydrolysis by known methods. If the involved prostaglandin is unstable towrd chemical hydrolysis, as with $PGE_2$ methyl ester, $PGD_2$ methyl ester, and the like, it is preferred to obtain the free acid by enzymatic hydrolysis, for example by using the process of U.S. Pat. No. 3,761,356.

With these limitations, and options for protecting concommitant by present hydroxy groups, selectively hydrolyzing the functionally protected hydroxy groups without hydrolyzing the desired lactone, separating undesired products from those desired, and modifying the lactones by subsequent chemistry obvious to those skilled in the art, such as oxidation, reduction, alkylation and the like, it is possible to prepare the 1,9- 1,11-, and 1,15-lactones of prostaglandins and of prostaglandin analogs of biological importance.

The preferred method for lactone function between the carboxyl group and the 9-, 11-, or 15-hydroxyl group is the method described by Corey et al., J. Am. Chem. Soc. 96, 5614 (1974), as further described by Corey et al., J. Am. Chem. Soc 97, 653 (1975) and as exemplified further herein. Optionally other methods may be used, if desired, such as those of Masamure et al., J. Am. Chem. Soc. 97, 3515 (1975) and Gerloch et al., Helv Chem. Acta 57, 2661 (1974).

The invention can be more fully understood by the following examples:

Infrared absorption is measured on a Perkin-Elmer Model 421 infrared spectrophotometer, using Nujoll mulls.

Nuclear magnetic resonance (NMR) spectra are recorded on a Varian A-60 spectrophotometer on deuterochloroform solutions with tetramethylsilane as an internal standard.

"Brine" herein refers to an aqueous saturated sodium chloride solution.

"Skellysolve B" is a mixture of isomeric hexanes.

EXAMPLE 1

$PGF_{2\alpha}$, 1,15-lactone

A solution of 5.5 g of $PGF_{2\alpha}$ and 1.79 g of 1-butaneboronic acid in 150 ml of methylene chloride was heated at reflux for 15 min. Then about half of the methylene chloride was removed by distillation at atmospheric pressure. Additional methylene chloride was added to bring the volume back to the original 150 ml. This cycle-distillation of methylene chloride followed by replacement with fresh methylene chloride was repeated three times, after which all the solvent was removed in vacuo to produce the 9,11-c yclic boronate of $PGF_{2\alpha}$ as a residue.

The residue was dissolved in 180 ml of anhydrous, oxygen-free xylene and treated with 5.128 g of 2,2'-dipyridyl disulfide followed by 6.27 g of triphenylphosphine. After 18 hours at 25° under a nitrogen atmosphere, thin layer chromatographic analysis of an aliquot (solvent: 10 acetic acid/10 methanol/80 chloroform) showed complete conversion to the pyridinethiol ester.

The xylene solution ws diluted with 300 ml of oxygen-free xylene and was added dropwise over 10 hours to 3.2 liters of vigorously stirred, refluxing xylene under a nitrogen atmosphere. After the addition was complete, 100 ml of xylene was distilled off and the solution was heated at reflux for 24 hours. The reaction mixture was then cooled and the xylene was removed in vacuo (35° bath temperature) to give a residue. The residue was taken up in 500 ml of tetrahydrofuran and treated with 10 ml of 30% hydrogen peroxide and 100 ml of saturated aqueous sodium bicarbonate. The three-phase mixture was stirred vigorously for 30 min. at 25°, then concentrated in vacuo to give a residue. The residue was taken up in brine/ethyl acetate and extracted thoroughly with ethyl acetate. The combined organic layer was washed with three portions of 1N aqueous potassium bisulfate, and once with water, aqueous sodium bicarbonate and brine. After drying over sodium sulfate, the solvent was removed to afford a viscous yellow oil which was chromatographed on 500 g of Mallinckrodt acid-washed CC-4 silca. The column was packed with 25% ethyl acetate/hexane and eluted (100 ml fractions) with 50% ethyl acetate/hexane. Fractions 26-40, containing the product and no prostaglandin-related impurities, were combined. The desired product was crystallized from 40 ml of 1:1 ether/hexane, thereby affording pure lactone, M.P. 110°-111°.

The lactone exhibited infrared absorption at 3500, 3370, 3290, 3010, 1700, 1320, 1310, 1290, 1260, 1105, 1080, 1055, 970, and 730 cm$^{-1}$ and NMR peaks at 6.00-5.75 (vinyl; multiplet; 2H), 5.75-4.95 (vinyl and C-15H; multiplet; 3H), 4.30-3.85 (C$\underline{H}$OH; multiplet; 2H) and 2.65 p.p.m. (OH; broad singlet; shifted downfield on cooling; 2H). The mass spectrum of the bis-trimethylsilyl derivative exhibited fragments at 480 (M+), 465 (M—CH$_3$), 436 (M—CO$_2$), 409 (M—C$_5$H$_{11}$), 390, 380, 364, 238, 217.

Anal. Calc'd. for $C_{20}H_{32}O_4$: C, 71.39; H, 9.59. Found: C, 70.73; H, 9.31.

In like manner, but substituting ethyl acetate hexane for ether/hexane for recrystallization, PGF$_{2\alpha}$ 1,15-lactone was obtained: m.p. 110.0°-111.7°; $[\alpha]_D^{EtOH}$ — 71°.

Anal.: Cal'd. for $C_{20}H_{32}O_4$: C, 71.39; H, 9.59. Found: C, 71.46; H, 9.80.

EXAMPLE 2

PGE$_2$, 1,15-lactone

A mixture of PGE$_2$ (352 mg), of triphenylphosphine (393 mg) and 2,2'-dipyridyl disulfide (330 mg) in 5 ml of dryn, oxygen-free xylene was stirred under nitrogen at room temperature for 18 hr. The reaction mixture was then diluted with 250 ml of xylene and heated at reflux for 2 hours. TLC analysis of an aliquot showed < 10% starting PGE$_2$, > 90% PGE$_2$ 1,15-lactone, ~ 2% PGA$_2$ and no PGA$_2$ lactone. The solvent was removed by evaporation at reduced pressure to give a residue which was partitioned between brine and ethyl acetate. The ethyl acetate extracts were washed with aqueous sodium bicarbonate and brine, dried-over sodium sulfate and concentrated to dryness under vacuum to afford PGE$_2$ 1,15-lactone.

The product was purified by chromatography on 70 g of neutral silica packed with 30% ethyl acetate/hexane and eluted (6.5 ml fractions) with 40% ethyl acetate/hexane. Those fractions containing the product were combined to afford purified PGE$_2$, 1,15-lactone. The purified product crystallized spontaneously. Crystallization from ethyl acetate/hexane gave product, m.p. 72°-74°. Recrystallization afforded PGE$_2$ 1,15-lactone of analytical purity, m.p. 74°-75°.

EXAMPLE 3

PGE$_2$, 1,15-Lactone from PGF$_{2\alpha}$, 1,15-lactone

A solution of 1.07 g of PGF$_2$=, 1,15-lactone in 45 ml of anhydrous acetone was cooled under nitrogen to between —45° and —40° and treated with 4.5 ml of trimethylsilyldiethylamine. After the addition was complete (2-3 min.), the mixture was stirred at —42° ± 2° C. for 2 hours, by which time TLC (25% ethyl acetate/hexane) showd only a trace of starting material. The reaction mixture was then cooled to —78°, diluted with 150 ml of precooled ether (—78°) and poured into ice/brine. After extraction with hexane, the combined organic layers were washed with aqueous sodium bicarbonate and brine, dried over anhydrous sodium sulfate and concentrated in vacuo to afford the mono-trimethylsily derivative of PGE$_{2\alpha}$, 1,15-lactone.

Collins reagent was prepared by adding 2.45 g of dry chromium trioxide in one portion to a stirred solution of 3.99 ml of anhydrous pyridine in 120 ml methylene chloride at 0°. The resulting dark red solution was stirred at 25° for 1 hour, then recooled to 0°.

The mono-trimethylsilyl derivative of PGF$_{2\alpha}$1,15-lactone (above) was dissolved in 6 ml of methylene chloride and added in one portion to the rapidly stirred Collins reagent. The ice bath was removed and the reaction mixture was allowed to stir for 20 min. longer. The mixture was then poured onto a column containing 150 g of neutral silica. With the aid of a house-vacuum, the column was eluted into a 2-liter round bottom flask with 1000 ml of ethyl acetate. Removal of the solvent gave PGE$_2$, 1,15-lactone, 11-trimethylsilyl ether.

The PGE$_2$, 1,15-lactone 11-trimethylsilyl ether was dissolved in 150 ml of methanol, diluted with 60 ml of aqueous 2.5% citric acid and stirred at 25° for 30 min. After removal of about half of the methanol at reduced pressure, the remaining solution was diluted with brine and extracted thoroughly with ethyl acetate. The combined extracts were washed with aqueous sodium bicarbonate and brine, dried over sodium sulfate and concentrated. The crude product crystallized on trituration and was recrystallized from ether/hexane to afford PGE$_2$, 1,15-lactone, m.p. 73°-76°. The infrared spectrum exhibited peaks at 3430, 1725, 1335, 1315, 1285, 1245, 1165, 1150, 1075, 1040, 990, 975 and 730 cm$^{-1}$ and the mass spectrum showed fragments at 334 (M+), 316 (M—H$_2$O), 298, 290, 263, 262, 245, 207, 208, 1654, 163.

Anal. Calc'd. for $C_{20}H_{30}O_4$: C, 71.82; H, 9.04. Found: C, 71.63; H, 9.30.

EXAMPLE 4

PGA$_2$, 1,15-Lactone

To a solution of PGE$_2$, 1,15-lactone (350 mg) in 10 ml of dry pyridine was added 4 ml of acetic anhydride. The solution was allowed to stand at 25° for 3 hours. TLC analysis (25% ethyl acetate/hexane) showed no starting material, only a single, less polar spot. The reaction mixture was cooled in an ice bath and treated dropwise over 15 min. with 20 ml of methanol. The temperature was allowed to rise to 25° over about 2 hours. After an additional 18 hrs. at 25°, the reaction mixture of ice, ether, water, and 70 ml of 2N aqueous potassium bisulfate and extracted thoroughly with ether. The combined extracts were washed with water, aqueous sodium bicarbonate and brine, dried over anhydrous sodium sulfate and concentrated in vacuo to afford PGA$_2$, 1,15-lactone as a residue.

The residue was purified by chromatography on 100 g of neutral silica, packed and eluted (8 ml fractions) with 15% ethyl acetate/hexane. Those fractions which contained the product (based on TLC) were combined to afford purified PGA$_2$, 1,15-lactone. This material crystallized on standing and was recrystallized from ether/hexane to afford a pure sample, m.p. 60°-61.5°. The NMR spectrum contained signals ($\delta_{TMS}^{CDCl_3}$) at 7.50-7.33 (C-11H; four-line pattern; 1H) an 6.27-6.06 p.p.m. (C-10H; four-line pattern; 1H). The mass spectrum had peaks at 316.2075 (Theory for $C_{20}H_{28}O_3$ = 316.2038), as well as m/e 298,288, 259,229, 198 and the infrared spectrum had peaks at 3010, 1715, 1705 1580, 1355, 1345, 1325, 1245, 1170, 1145, 1140, 1035 and 970 cm$^{-1}$.

EXAMPLE 5

PGA$_2$, 1,15-lactone

Following the procedure of example 2, but substituting PGA$_2$ for PGE$_2$ there is produced a crude product containing PGA$_2$ 1,15-lactone and several impurities.

The crude product is purified by repeated chromatography and crystallization to afford as a purified product PGA$_2$, 1,15-lactone identical to the material produced by the procedure of Example 4.

EXAMPLE 6

17-Phenyl-18,19,20-trinor-PGF$_{2\alpha}$, 1,15-lactone

A solution of 17-phenyl-18,19,20-trinor-PGF$_{2\alpha}$ (776 mg) and 1-butaneboronic acid (225 mg) in 25 ml of methylene chloride was heated at reflux. After 15 min the methylene chloride was allowed to distill off slowly. Fresh methylene chloride was added when the total volume was reduced to about one-half of the original volume. After 90 minutes, all of the methylene chloride was removed in vacuo to afford cyclic boronate of the starting prostaglandin.

The cyclic boronate was dissolved in 5 ml of anhydrous, oxygen free xylene and was treated with 2,2'-dipyridyl disulfide (660 mg) and triphenylphosphine (786 mg). After 4 hours at 25° the reaction mixture was diluted with 500 ml of anhydrous, oxygen-free xylene and was heated at reflux for 18 hr. The xylene was removed in vacuo to give a residue. The residue was taken up in 50 ml of tetrahydrofuran containing 1 ml of 30% aqueous hydrogen peroxide (11.6 mmoles) and treated at 25° with a solution of sodium bicarbonate (1.68 g) in 10 ml of water. This mixture was stirred vigorously for 30 min, then concentrated under reduced pressure to give a residue. The residue was taken up in brine/ethyl acetate and extracted thoroughly with ethyl acetate. The combined extracts were washed with aqueous sodium bisulfate, water, aqueous sodium bicarbonate and brine, then dried over sodium sulfate and concentrated to afford a residue of crude 17-phenyl-18,19,20-trinor PGF$_{2\alpha}$, 1,15-lactone.

The crude lactone was purified by chromatography on 400 g of neutral silica packed and eluted (22 ml fractions) with ethyl acetate. The fractions which contained the product, based on TLC, were combined yielding purified 17-phenyl-18,19,20-trinor-PGF$_{2\alpha}$, 1,15-lactone. The lactone crystallized upon trituration and after two recrystallizations from ethyl acetate/hexane exhibited m.p. 116°-117°.

The infrared spectrum exhibited peaks at 3460, 3400 sh, 3020, 1705, 1650, 1605, 1495, 1325, 1300, 1265, 1150, 1100, 1040, 1020, 1000, 970 and 700 cm$^{-1}$ and the mass spectrum showed fragments at m/e 370 (M-18), 352, 334, 308, 298, 261, 243, 225. (No M+ peak was apparent.)

Anal. Calc'd. for $C_{23}H_{30}O_4$: C, 74.56; H, 8.16. Found: C, 74.27; H, 7.97.

EXAMPLE 7

17-Phenyl-18,19,20-trinor-PGE$_2$, 1,15-lactone

A solution of 17-phenyl-18,19,20-trinor-PGE$_2$ (735 mg), 2,2'-dipyridyldisulfide (628 mg) and triphenylphosphine (748 mg) in 10 ml of anhydrous, oxygen-free xylene was stirred at 25° in an atmosphere of nitrogen for 2 hr. The mixture was then diluted with 400 ml of anhydrous, oxygen-free xylene, heated at reflux for 2.5 hrs, and evaporated under vacuum at 30° to give a residue. The residue was chromatographed on 100 g of neutral silica, packed and eluted (8 ml fractions) with 80% ether/hexane. The fractions containing homogeneous product by TLC were combined to afford purified 17-phenyl-18,19,20-trinor-PGE$_2$, 1,15-lactone. Two recrystallizations from ether/hexane afforded pure product, m.p. 81°-83°. The infrared spectrum exhibited peaks at 3440, 3000, 1725, 1605, 1330, 1240, 1160, 1145, 1085, 1045, 975, 745, 725 and 700 cm$^{-1}$ and the mass spectrum showed fragments at m/e 368 (M-18), 350, 332, 297, 296, 277, 259, 241 (no M+ apparent).

EXAMPLE 8

16-Phenoxy-17,18,19,20-tetranor-PGF$_{2\alpha}$1,15-lactone

Following the procedure of example 1 but substituting 16-phenoxy-17,18,19,20-tetranor PGF$_{2\alpha}$ for PGF$_{2\alpha}$ there was produced a crude product of 16-phenoxy-17,18,19,20-tetranor-PGF$_{2\alpha}$, 1,15-lactone as a viscous yellow oil.

The crude product was purified by chromatography over neutral silica packed in 50% ethyl acetate/hexane and eluted with 50% ethyl acetate/hexane followed by 70% ethyl acetate hexane. Those fractions containing homogeneous product as judged by TLC were combined to afford crystalline 16-phenoxy-17,18,19,20-tetranor-PGF$_{2\alpha}$, 1,15-lactone. The lactone thus obtained was recrystallized from ethyl acetate/hexane to afford pure product, m.p. 185°-186°. The mass spectrum of the trimethylsilyl derivative exhibited a peak at M+ 516.2738 (theory for $C_{28}H_{44}Si_2O_5$: 516.2727) and fragments at m/e 50M, 426, 423, 409, 400, 333, 307, 217 and 181.

EXAMPLE 9

PGF$_{1\alpha}$, 1,15-lactone and 15-epi-PGF$_{1\alpha}$, 1,15-lactone

Following the procedure of Example 1 but substituting PGF$_{1\alpha}$ for PGF$_{2\alpha}$ there was obtained a crude product containing PGF$_{1\alpha}$, 1,15-lactone as a viscous yellow oil.

The crude product was purified by chromatography on 700 g of neutral silica, packed and eluted with 50% ethyl acetate/hexane. The first 2 liters of eluate were discarded, after which 100 ml fractions were collected.

A minor product eluted first from the column (fractions 14-19) which was homogeneous by TLC was combined to give 15-epi-PGF$_{2\alpha}$, 1,15-lactone [(15R)-PGF$_{2\alpha}$, 1,15-lactone]. The infrared spectrum exhibited peaks at 3450, 1730, 1585, 1250, 1100, 970 and 735 cm$^{-1}$ and the NMR spectrum showed peaks ($\delta_{TMS}^{CDCl_3}$) at 5.85–5.05 (vinyl and C-15; multiplet; 3H; 4.25–3.85 (CHOH; multiplet; 2H) and 3.30 ppm (singlet, shifts downfield when sample is cooled; OH; 2H).

The major product, eluted later from the column (fractions 21–28), were combined to afford purified PGF$_{1\alpha}$, 1,15-lactone. The purified PGF$_{1\alpha}$1, 1,15-lactone crystallized upon trituration with ether, and recrystallization (ethyl acetate/hexane) afforded a pure sample, m.p. 105°–106°. The infrared spectrum exhibited peaks at $\nu$max 3520, 3480, 3380, 1710, 1300, 1290, 1265, 1250, 1235, 1160, 1100, 1075, 1055, 1000 and 965 cm$^{-1}$. The NMR spectrum showed peaks ($\delta_{TMS}^{CDCl_3}$) at 6.0–5.75 (vinyl; multiplet; 2H; 5.60–5.00 (C-15H; multiplet; 1H9, 4.25–3.80 (CHOH; multiplet; 2H) and 3.08 ppm (OH singlet, shifts downfield on cooling; 2H), and the mass spectrum showed fragments at 338 (M+), 320, 302, 266, 249, 231.

Anal. Calc'd. for $C_{20}H_{34}O_4$: C, 70.97; H, 10.13. Found: C, 70.56; H, 10.25

Saponification of 100 mg of 15-epi PGF$_{1\alpha}$, 1,15-lactone in 3 ml of methanol with a solution of 3 ml of 3N potassium hydroxide under nitrogen for 2 hours at 25° followed by acidification, extraction, and evaporation to dryness afforded crystalline 15-epi PGF$_{1\alpha}$ in nearly quantitative yield, identical with an authentic sample.

EXAMPLE 10

PGE$_1$ 1,15-lactone

Following the procedure of Example 2 but substituting PGE$_1$ for PGE$_2$ there is produced, after chromatography on neutral silica purified PGE$_1$, 1,15-lactone, which crystallized on standing. Recrystallization from ether/hexane afforded pure PGE$_1$ 1,15-lactone, m.p. 89°–90°.

EXAMPLE 11

PGE$_1$ 1,15-lactone from PGF$_{1\alpha}$ 1,15-lactone

Following the procedure of example 3 but substituting PGF$_{1\alpha}$1,15-lactone for PGF$_{2\alpha}$, 1,15-lactone, there is produced a crude product containing PGE$_1$ 1,15-lactone. Chromatography of the crude PGE$_1$, 1,15-lactone over neutral silica packed in 20% ethyl acetate/hexane and eluted with 40% ethyl acetate hexane afforded purified PGE$_1$ 1,15-lactone which, on recrystallization from ether/hexane afforded pure PGE$_1$ 1,15-lactone, m.p. 87°–88° identical to that produced by the procedure of example 10.

The infrared spectrum exhibited peaks at 3390, 3320 sh, 1745, 1720, 1335, 1255, 1235, 1195, 1180, 1160, 1100, 1075 and 980 cm$^{-1}$; the NMR spectrum exhibited peaks ($\delta_{TMS}^{CDCl_3}$) at 6.1–5.85 (vinyl; multiplet; 2H), 5.45–5.05 (C-15H; multiplet; 1H), and 4.40–3.85 ppm (C-11H; multiplet; 1H); and the mass spectrum of the trimethylsilyl ether showed M+ 408.2694 (theory for $C_{23}H_{40}SiO_4$ = 408.2696) as well as peaks at m/e 393, 390, 380, 375, 365, 364, 318, 264, 150 and 99.

Anal. Calc'd. for $C_{20}H_{32}O_7$: C, 71.39; H, 9.59. Found: C, 71.02; H, 9.36.

EXAMPLE 12

13,14-Didehydro-8$\beta$,9$\beta$,11$\beta$,12$\alpha$-PGF$_{2\alpha}$ 1,15-lactone and 13,14-didehydro PGF$_{2\alpha}$ 1,15-lactone Following the procedure of example 1 but substituting 13,14dehydro-8$\beta$,9$\beta$,11$\beta$,12$\alpha$ PGF$_{2\alpha}$ [also known as ent-13-dehydro-15-epi-prostaglandin F$_{2\alpha}$ (compound 2 of J. Fried and CHLin, J. Med. Chem. 16, 429 (1973) and 13,14-didehydro PGF$_{2\alpha}$ for PGF$_{2\alpha}$, there are produced 13,14-didehydro-8$\beta$,9$\beta$,11$\beta$,12$\alpha$-PGF$_{2\alpha}$1,15-lactone and 13,14-didehydro-PGF$_{2\alpha}$ 1,15-lactone, respectively.

EXAMPLE 13

13,14-didehydro-8$\beta$,11$\beta$,12$\alpha$-PGE$_2$ 1,15-lactone and 13,14-didehydro-PGE$_2$ 1,15-lactone Following the procedure of example 2 but substituting 13,14-didehydro-8$\beta$,11$\beta$,12$\alpha$-PGE$_2$ [also known as ent-13-dehydro-15-epi-PGE$_2$ (from 2a of J. Fried and C. H. Lin, J. Med. Chem. 16 429 (1973) and 13,14-didehydro PGE$_2$ for PGE$_2$ there are produced 13,14-didehydro-8$\beta$,11$\beta$,12$\alpha$-PGE$_2$ 1,15-lactone and 13,14-didehydro PGE$_2$ 1,15-lactone, respectively.

EXAMPLE 14

13,14-dihydro PGF$_{2\alpha}$ 1,15-lactone

Following the procedure of example 1 but substituting 13,14-dihydro PGF$_{2\alpha}$ for PGF$_{2\alpha}$, there is produced 13,14-dihydro PGF$_{2\alpha}$ 1,15-lactone.

EXAMPLE 15

(15S)-15-methyl PGF$_{2\alpha}$ 1,15-lactone

Following the procedure of example 1 but substituting (15S) 15-methyl PGF$_{2\alpha}$ for PGF$_{2\alpha}$ and extending the reaction time in refluxing xylene from 24 hours to 48 hours there is produced crude (15S)-15-methyl PGF$_{2\alpha}$, 1,15-lactone. The crude lactone is purified by repeated chromatography and, further, if desired, by TLC purification to afford in low yield (15S)-15-methyl-PGF$_{2\alpha}$, 1,15-lactone in essentially pure form.

EXAMPLE 16

16,16-dimethyl-PGF$_{2\alpha}$ 1,15-lactone

Following the procedure of example 15 but substituting 16,16-dimethyl PGF$_{2\alpha}$ for (15S) 15-methyl PGF$_{2\alpha}$ there is produced 16,16-dimethyl PGF$_{2\alpha}$, 1,15-lactone.

EXAMPLE 17

Following the procedure of example 8 but substituting 16-m-trifluoromethylphenoxy-17,18,19,20-tetranor PGF$_{2\alpha}$, 16-m-chlorophenoxy-17,18,19,20-tetranor PGF$_{2\alpha}$, and 16-p-fluorophenoxy-17,18,19,20-tetranor PGF$_{2\alpha}$ for 16-phenoxy-17,18,19,20-tetranor PGF$_{2\alpha}$ there are obtained the corresponding 1,15-lactones.

EXAMPLE 18

Following the procedure of example 2 but substituting (16S) 16-methyl-, (16R) 16-methyl- and 16-methylene PGE$_2$ for PGE$_2$ there are produced, respectively, the corresponding (16S) 16-methyl, (16R) 16-methyl-, and 16-methylene PGE$_2$ 1,15-lactones.

EXAMPLE 19

16,16-dimethyl PGE$_2$ 1,15-lactone

Following the procedure of example 3 but substituting 16,16-dimethyl PGE$_{2\alpha}$ 1,15-lactone for PGF$_{2\alpha}$ 1,15-lactone there is produced 16,16-dimethyl PGE$_2$ 1,15-lactone.

EXAMPLE 20

(15S) 15-methyl PGE$_2$ 1,15-lactone

Following the procedure of example 3 but substituting (15S) 15-methyl PGF$_{2\alpha}$ 1,15-lactone for PGF$_{2\alpha}$ 1,15- lactone, there is produced (15S) 15-methyl PGE$_2$ 1,15-lactone.

EXAMPLE 21

11-deoxy PGE$_2$ 1,15-lactone

Following the procedure of example 2 but substituting 11-deoxy PGE$_2$ for PGE$_2$ there is produced 11-deoxy PGE$_2$ 1,15-lactone.

In like manner, substituting 11-deoxy PGE$_1$ for PGE$_1$ affords PGE$_1$, 1,15-lactone.

EXAMPLE 22

(15S) 11-deoxy-15-methyl PGE$_2$ 1,15-lactone and 11-deoxy-16,16-dimethyl PGE$_2$, 1,15-lactone Following the procedure of example 2 but substituting (15S) 11-deoxy-15-methyl PGE$_2$ and 11-deoxy-16,16-dimethyl PGE$_2$ for PGE$_2$ and extending the reflux period in xylene from 2 hours to 48 hours there are produced the corresponding 1,15-lactones. The crude lactones are purified by repeated chromatography and further, if desired, by TLC purification to afford in low yield (15S) 11-deoxy-15-methyl PGE$_2$ 1,15-lactone and 11-deoxy-16,16-dimethyl PGE$_2$ 1,15-lactone, respectively, in essentially pure form.

EXAMPLE 23

11-deoxy PGF$_{2\alpha}$ 1,15-lactone

A solution of 11-deoxy PGE$_2$ 1,15-lactone (0.5 g) in methanol (50 ml) is treated at 0° with sodium borohydride (500 mg) added in 50 mg portions every 2 minutes. Aqueous sodium bisulfate (1M) is added until the mixture is acidic and the product is isolated by extraction with ethyl acette. The extract is washed, dried, and concentrated to yield a residue containing 11-deoxy PGF$_{2\alpha}$, 1,15-lactone.

The residue is purified by chromatography over acid-washed silica using 1% ethyl acetate/hexane increasing to 40% ethyl acetate/hexane. Those fractions containing homogeneous product as judged by TLC and by saponification to the known 11-deoxy PGF$_{2\alpha}$ are combined to afford 11-deoxy PGF$_{2\alpha}$, 1,15-lactone in essentially pure form.

In like manner, substituting (15S) 11-deoxy-15-methyl PGF$_{2\alpha}$ 1,15-lactone, 11-deoxy-16,16-dimethyl PGE$_2$ 1,15-lactone PGE$_2$, 1,15-lactone, (15S) 15-methyl PGE$_2$ 1,15-lactone, 16,16-dimethyl PGE$_2$ 1,15-lactone and PGE$_1$ 1,15-lactone and PGE$_1$ 1,15-lactone for 11-deoxy PGE$_2$ 1,15-lactone there are produced the 1,15-lactones of (15S) 11-deoxy 15-methyl PGF$_{2\alpha}$, 11-deoxy-16,16-dimethyl PGF$_{2\alpha}$, PGF$_{2\alpha}$, (15S) 15-methyl PGF$_{2\alpha}$, and PGF$_{1\alpha}$, respectively.

EXAMPLE 24

PGD$_2$ 1,15-lactone

A. To a solution of PGF$_{2\alpha}$ 1,15-lactone (1.0 g) in 3 ml of anhydrous dimethylformamide at 0° was added with stirring a solution of t-butyldimethylsilyl chloride (474 mg) and imidazole (428 mg) in 3 ml of dimethylformamide. The mixture was stirred for 1 hr at 0° under nitrogen, then poured into brine and extracted with hexane. The extract was washed with water, cold dilute aqueous sodium bisulfate, wate, aqueous sodium bicarbonate and brine, dried over sodium sulfate and concentrated in vacuo to afford a residue containing PGF$_2\alpha$1,15-lactone 11-t-butyldimethylsilyl ether.

The residue was purified by chromatography on 140 g of neutral silica packed with 5% ethyl acetate/hexane and eluted (12 ml fractions) with 20% ethyl acetate/hexane. Those fractions which were homogeneous by tlc (fractions 44-56) were combined to give PGF$_2\alpha$, 1,15-lactone, 11-t-butyldimethylsilyl ether with an infrared spectrum showing peaks at 3500, 1730, 1460, 1240, 1125, 1110, 1040, 1005, 975, 880, 854, 840 and 780 cm$^{31 1}$ and an NMR spectrum with peaks ($\delta_{TMS}^{CDCL3}$) at 5.90-4.94 (vinyl and C-15H; multiplet; 5H), 4.25-3.75 (C$\underline{H}$O; multiplet; 2H), 3.70 (OH; broad singlet which shifts downfield on cooling; 1H), 0.85 (tBu; singlet; 9H) and 0 ppm (SiC$\underline{H}_3$; singlet; 6H).

B. A solution of PGF$_2$60 , 1,15-lactone, 11-tbutyldimethylsilyl ether (1.05 g), freshly distilled dihydropyran (5 ml), and pyridine hydrochloride (50 mg) in 25 ml of anhydrous methylene chloride was stirred under nitrogen at 25° for 18 hr. The reaction mixture was poured into ice/sodium bicarbonate/water and extracted thoroughly with hexane. The extract was washed with brine, dried over sodium sulfate and concentrated in vacuo to afford a residue.

The residue was purified by chromatography on 140 g of neutral silica packed with 5% ethyl acetate/hexane and eluted (12 ml fractions) with 10% ethyl acetate/hexane. Those fractions which were homogeneous by TLC (fractions 34-48) were combined to give pure PGF$_2\alpha$, 1,15-lactone, 9-tetrahydropyranyl ether, 11-t-butyldimethylsilyl ether was infrared bands at 1740, 1460, 1350, 1240, 1140, 1120, 1040, 1020, 990, 975, 860, 840 and 780 cm$^{-1}$ and an NMR spectrum with peaks ($\delta_{TMS}^{CCl_4}$) at 5.95-5.0 (vinyl and C-15; multiplet; 5H), 4.75-4.50 (—O—C$\underline{H}$—O of THP; multiplet; 1H), 4.30-3.25 (C$\underline{H}$O at C-9, C-11 and THP; multiplet; 4H), 0.88 (tBu; singlet; 9H) and 0 pm (SiC$\underline{H}_3$; singlet; 6H).

C. To a stirred solution of PGF$_2\alpha$, 1,15-lactone, 9-tetrahydropyranyl ether, 11-t-butyldimethylsilyl ether (1.17 g) in 5 ml of anhydrous tetrahydrofuran at 25° was added under nitrogen in one portion 22 ml of a 0.3 M solution of tetrabutylammonium fluoride in tetrahydrofuran. The reaction mixture was stirred for 30 min at 25°, then poured into a mixture of ice/water/sodium bicarbonate/hexane and extracted thoroughly with hexane. The extract was washed with brine, dried over sodium sulfate and evaporated to afford a residue of PGF$_2\alpha$, 1,15-lactone-9-tetrahydropyranyl ether. The residue appeared to be essentially pure by tlc (30% ethyl acetate/hexane) and was oxidized directly without further purification. However, for purposes of characterization, a 75 mg sample of the thus obtained residue was chromatographed on a column of 15 g of neutral silica packed with 10% ethyl cetate/hexane and eluted with 100 ml of the same solvent followed by 2% ethyl acetate/hexane.

The pure PGF$_2\alpha$, 1,1,5-lactone, 9-tetrahydropyranyl ether thus obtained exhibited infrared peaks at 3500, 1730, 1440, 1340, 1240, 1200, 1160, 1140, 1120, 1080, 1040, 1020, 990, 970, 920, 870, 815 and 735 cm$^{-1}$ and NMR peaks ($\delta_{TMS}^{CDCl_3}$) at 6.0-5.0 (vinyl and C-15; multiplet; 5H), 5.75-5.0 (O—C$\underline{H}$—O of THP; multiplet; 1H), 4.35-3.30 (C$\underline{H}$O at C-9, C-11 and THP; multiplet; 4H) and 2.35 ppm (O$\underline{H}$; singlet which broadens and shifts downfield on cooling; 1H).

D. The residue of PGF$_2\alpha$, 1,15-lactone, 9-tetrahydropyranyl ether (920 mg) was dissolved in 30 ml of reagent grade acetone, cooled to between −20° and −30°, and treated dropwise with 0.8 ml of Jones reagent (J. Org. Chem. 21, 1547, 1956). After 75 min at −25° ± 5°, isopropyl alcohol (0.5 ml) was added. After an additional 10 min at −25°, the mixture was diluted with 400 ml of water and extracted thoroughly with 4:1 hexane:ethyl acetate. The extract was washed with water, ice cold aqueous sodium bisulfate, water, aqueous sodium bicarbonate and brine, dried over sodium sulfate and concentrated in vacuo to afford a residue.

The residue was purified by chromatography on 140 g of neutral silica packed with 5% ethyl acetate/hexane and eluted with 20% ethyl acetate/hexane. After discarding the first 300 ml of eluate, 12 ml fractions were collected. Those fractions containing homogeneous product by TLC (fractions 21-35) were combined to yield pure $PGD_2$, 1,15-lactone, 9-tetrahydropyranyl ether with infrared peaks at 1745, 1460, 1440, 1370, 1340, 1240, 1200, 1160, 1140, 1120, 1080, 1040, 1020, 995, 980, 920, 870, 815 and 735 cm$^{-1}$ and with NMR peaks ($\delta_{TMS}^{CDCl_3}$) at 5.90-5.0 (vinyl and C-15; multiplet; 5H) and 4.80-3.40 ppm (C$\underline{H}$O; broad muliplets; 4H).

E. A mixture of $PGD_2$, 1,15-lactone, 9-tetrahydropyranyl ether (700 mg) in 33 ml of tetrahydrofuran, 33 ml of water and 66 ml of acetic acid was stirred and heated at 40° for 3 hr. The reaction mixture was then cooled to below room temperature, poured into 1:1 brine/water and extracted thoroughly with 1:1 ethyl acetate/hexane. The combined extract was washed with aqueous sodium bicarbonate and brine, dried over sodium sulfate and evaporated to give a esidue containing $PGD_2$ 1,15-lactone.

The residue crystallized on trituration with ether/hexane mixtures and was purified by careful recrystallization from ether/hexane to give pure $PGD_2$ 1,15-lactone, m.p. 93°-94° C.

EXAMPLE 25

Prostaglandin $B_2$, 1,15-lactone

A solution, prepared by the consecutive addition of $PGB_2$ (0.334 g), 5 ml of dry nitrogen-purged xylene, triphenylphosphine (0.393 g) and 2,2'-dipyridyldisulfide, (0.330 g) was stirred at room temperature under a nitrogen atmosphere for 6 hr. The mixture was then diluted with 250 ml of dry nitrogen-purged xylene, heated under reflux for 16 hr, and concentrated in vacuo at a bath temperature of 40° to afford a residue. The residue was purified by chromatograhy in a dry-packed column of 100 g of silica gel and 20 ml of ether. The column was eluted with 60% ether in hexane and 20-ml fractions were collected. Those fractions homogeneous by TLC were combined to give pure $PGB_2$, 1-15-lactone, with Rf of 0.37 on a silica gel plate developed with 1:1 ether-hexane.

The mass spectrum exhibited key ion peaks at m/e 316.2021 (theor. for $C_{20}H_{26}O_3$ 316.2038), 298, 288, 269, and 217.

The NMR spectrum of the product shows key signals ($\delta_{TMS}^{CDCl_3}$) at about 5.97-6.80 (multiplet, conj. —CH= • CH—), 5.07-5.70 multiplet, unconj. —CH=CH— and C-15 H) and 2.83-3.12 (multiplet, C-7 $CH_2$).

EXAMPLE 26

$PGF_2\alpha$, 1,9-Lactone

To a solution of $PGF_2\alpha$, 11,15-bis($\alpha$-ethoxyethyl ether) (496 mg) in 5 ml of anhydrous oxygen-free xylene was added 2,2'-dipyridyl disulfide (330 mg) and triphenylphosphine (393 mg). The solution was stirred 2.5 hr at 25° under an atmosphere of nitrogen, diluted with 250 ml of dry, oxygen-free xylene, and heated at reflux for 18 hr. Removal of xylene under vacuum at 30° afforded a residue which was diluted with aqueous sodium bicarbonate and extracted with hexane. The combined hexane layers were washed with brine, dried over anhydrous sodium sulfate and concentrated to yield a residue containing $PGF_2\alpha$ 1,9-lactone bis($\alpha$-ethoxyethyl ether).

The residue was dissolved in 40 ml of tetrahydrofuran and 30 ml of water, treated with 6 ml of 85% phosphoric acid, and stirred under nitrogen at 40° for 2.5 hr. Most of the tetrahydrofuran was evapoated at reduced pressure and the concentrate was diluted with ethyl acetate and aqueous sodium bicarbonate. The product was isolated by extraction with ethyl acetate. The combined organic layer was washed with aqueous sodium bicarbonate and brine, dried over magnesium sulfate and concentrated to yield crude $PGF_2\alpha$ 1,9-lactone. The crude lactone was purified by chromatography on 50 g of neutral silica packed with 1:1 ethyl acetate/hexane and eluted (7 ml fractions) with pure ethyl acetate.

Those fractions containing product (27-82) were combined, yielding a partially purified product which was still contaminated on TLC analysis with a UV-visible, vanillin-invisible spot. The partially purified material was rechromatographed on 50 g of silica packed in 10% acetone/methylene chloride and eluted (7 ml fractions) as follows:

200 ml 10% acetone/methylene chloride
1500 ml 20% acetone/methylene chloride
1500 ml 35% acetone/methylene chloride Those fractions containing homogeneous product by TLC analysis were (combined) to yield pure $PGF_2\alpha$, 1,9-lactone which crystallized on standing and was recrystallized from ethyl acetame/hexane, m.p. 87.1°-88.8° (change of crystal form at 44°-45°).

The infrared spectrum exhibited peaks at 3460, 3000, 1730, 1705, 1335, 1285, 1230, 1210, 1180, 1150, 1085, 1065, 1025, 970 and 720 cm$^{-1}$ and the mass spectrum showed peaks at m/e 318 (M-18) 300, 289, 274, 247, 229, 219, 192 (no M$\rightleftarrows$ Apparent).

A sample of this product (2 mg) was hydrolyzed using 0.5 ml of methanol and 0.5 ml of 3N aqueous sodium hyroxide. After 2 hr at 25°, the mixture was acidified and extracted with ethyl acetate. After drying, concentration of the extracts gave approx. 2 mg. By tlc, this crude product consisted of > 99% of $PGF_2\alpha$. No other isomer was detectable in the following solvent systems: ALX and 5 HOAc/10 MeOH/85 $CHCl_3$ — using regular silica plates, silver nitrate impregnated plates.

Hydrolysis of a 2 mg sample in 0.5 ml methanol and 0.5 ml 3N aqueous sodium hydroxide afforded pure $PGF_2\alpha$, idendentical with an authentic sample.

EXAMPLE 27

(15S)-15-methyl-$PGF_{2\alpha}$, 1,9-lactone

A solution of (15S)-15-methyl-$PGF_{2\alpha}$(184 mg) in 2.5 ml of anhydrous, oxygen-free xylene containing 2,2'-dipyridyl disulfide (165 mg) and triphenylphosphine (196 mg) was stirred under nitrogen for 2.5 hr at 25°. The mixture was diluted with 150 ml of xylene and heated at reflux for 3 hr. TLC (80% EtOAc/hexane) showed essentially a single less polar product. The xylene was removed by evaporation at reduced pressure to afford a residue which was diluted with ice/water/sodium bicarbonate and ethyl acetate and extracted thoroughly with ethyl acetate. The ethyl acetate extract was washed with brine, dried over anhydrous sodium sulfate and concentrated to afford a residue (15S)-15- methyl $PGF_{2\alpha}$, 1,9-lactone. The residue was purified by chromatography on 50 g of neutral silica packed with 10% acetone/methylene chloride and eluted (5 ml fractions) with 200 ml of 10% acetone/methylene chloride, 1500 ml of 20% acetone/methylene chloride and 1000 ml of 35% acetone/methylene chloride.

Those fractions containing homogeneous product by TLC assay (fractions 135–229) were combined to yield pure (15S)-15-methyl-$PGF_{2\alpha}$, 1,9-lactone.

The product exhibited infrared peaks at 3400, 3000, 2960, 2920, 2860, 1740, 1715, 1450, 1370, 1350, 1265, 1225, 1205, 1180, 1145, 1125, 1085, 1030, 970, 935, 905 and 715 $cm^{-1}$ and the mass spectrum showed peaks at m/e 350 (M+), 332 (M-18) 314, 303, 288, 261, 243.

Saponification of a 2 mg sample of (15S)-15-methyl $PGF_{2\alpha}$, 1,9-lactone in 1 ml of methanol and 1 ml of 3N aqueous potassium hydroyide for 2 hours at room temperature followed by esterification with diazomethane afforded (15S)-15-methyl $PGF_{2\alpha}$ methyl ester, identical with an authentic sample and free of contamination with (15R) 15-methyl $PGF_{2\alpha}$ methyl ester.

In like manner, but substituting (15R)-15-methyl $PGF_{2\alpha}$ for (15S)-15-methyl $PGF_{2\alpha}$, there is produced (15R)-15-methyl $PGF_{2\alpha}$ 1,9-lactone.

EXAMPLE 28

(15S)-15-methyl-$PGF_{2\alpha}$, 1,9-lactone

A solution of (15S)-15-methyl $PGF_{2\alpha}$ (368 mg) in 1 ml of pyridine was treated at 0° with acetic anhyride (0.2 ml) and the resulting solution was stirred at 0° for 3 hours and 25° for 1 hour. The reaction mixture was diluted with 0.18 ml of water and was stirred 18 hours at 25°. The mixture was then poured intoice/brine/ethyl acetate/dil aqueous sodium bisulfate and extracted with ethyl acetate. The extract was washed with brine, dried over sodium sulfate and concentrated to give a residue containing the 11-mono and 9,11-diacetate. The residue was chromatographed over 70 g of acid-washed silica. The column was eluted (5 ml fractions) with 1000 ml of 35% ethyl acetate/hexane.

Fractions 81–115 afforded pure (15S)-15-methyl-$PGF_{2\alpha}$, 9,11-diacetate with infrared peaks at 3450, 2600, 1745, 1725, 1370, 1240, 1040, 970 $cm^{-1}$ and NMR peaks ($\delta_{TMS}^{CDCL_3}$) at 6.7 (O$\underline{H}$; singlet which shifts downfield on cooling; 2H9, 5.7–4.7 (vinyl and C$\underline{H}$OAc; multiple 6H), 2.06 and 2.00 (OCOC$\underline{H}_3$; two singlets; 3H each) and 1.28 ppm (C$\underline{H}_3$; singlet; 3H).

Further elution of the above chromatogram with 65% ethyl acetate/hexane afforded pure (15S)-15-methyl-$PGF_{2\alpha}$, 11-acetate with infrared peaks at 3500, 3200, 2700, 1750, 1725, 1370, 1240, 1040, 975 $cm^{-1}$ and NMR peaks ($\delta_{TMS}^{CDCl_3}$) at 5.65–5.10 (vinyl multiplet; 4H), 4.28 (O$\underline{H}$; singlet; 3H—shifts downfield on cooling), 5.1–4.65 (C$\underline{H}$OAc; multiplet; 1H) 4.20 (C$\underline{H}$OH; apparent riplet, J = 4.5 Hz; 1H) 2.00 (OC$\underline{O}$C$\underline{H}_3$; singlet; 3H) and 1.26 ppm (15—C$\underline{h}_3$; singlet; 3H).

A solution of (15S)-15-methyl-$PGF_{2\alpha}$, 11-acetate (120 mg), triphenylphosphine (115 mg) and 2,2'-dipyridyl disulfide (97 mg) in 3 ml of dry, oxygen-free xylene was stirred 18 hr at 25° under a nitrogen atmosphere. The mixture was then diluted with 150 ml of xylene and heated at reflux for 60 min. The xylene was removed in vacuo to afford a residue which was partioned between hexane and aqueous sodium bicarbonate. The hexane layer was washed with brine, dried over sodium sulfate and evaporated to afford a residue of crude (15S)-15-methyl $PGF_\alpha$ 1,9-lactone 11-acetate.

The residue was purified by chromatography on 50 g of neutral silica, packed and eluted with 10% acetone/methylene chloride (12 ml fractions).

Those fractions containing pure product by TLC analysis (fractions 17–28) were combined to give pure (15S) 15-methyl $PGF_{2\alpha}$ 1,9-lactone 11-acetate.

A mixture of 80 mg of (15S)-15-methyl-$PGF_{2\alpha}$ 1,9-lactone, 11-acetate and 1 g of sodium bicarbonate in 16 ml of 1:1 methanol/water was stirred at 40° + 2° under nitrogen for 48 hr. TLC (65% ethyl acetate hexane) showed essentially a single more polar spot. The mixture was cooled, diluted with brine and extracted thoroughly with ethyl acetate. The combined extract was washed with brine, dried with sodium sulfate and concentrated to give crude (15S)-15-methyl 1,9-lactone $PGF_{2\alpha}$. The crude product was purified by chromatography on 15 g of neutral silica, packed with 20% ethyl acetate/hexane. The column was eluted (3 ml fractions) with 60% ethyl acetate/hexane.

Those fractions which contained homogeneous product (fractions 194–234) were combined to yield pure (15S)-15-methyl $PGF_{2\alpha}$, 1,9-lactone identical in its properties to the material prepared by the procedure of example 27.

EXAMPLE 29

(15S)-15-Methyl-17-phenyl-18,19,20-trinor-$PGF_{2\alpha}$ 1,9-lactone

A solution of 15-methyl-17-phenyl-18,19,20-trinor-$PGF_{2\alpha}$ (474 mg) in 10 ml of benzene was treated with triphenylphosphine (464 mg) and 2,2'-dipyridyl disulfide (390 mg). The resulting yellow solution was stirred for 2 hr at 25° under nitrogen, then diluted with 250 ml of anhydrous, oxygen-free benzene and heated at reflux for 24 hr. The benzene was removed in vacuo to afford a residue which was chromatographed on 60 g of neutral silica packed with 10% acetone/methylene chloride and eluted with 300 ml of 10% acetone/methylene chloride followed by 1000 ml of 20% acetone/methylene chloride (fraction size approx. 7 ml).

Those fractions containing homogeneous product by TLC analysis (fractions 80–95) were combined, affording pure (15S)-15-methyl-17-phenyl-18,19,20-trinor-$PGF_{2\alpha}$ 1,9-lactone with infrared peaks at 3400, 3060, 2960, 2940, 2860, 1735, 1710, 1605, 1495, 1450, 1365, 1345, 1265, 12225, 1180, 1145, 1115, 1085, 1030, 975, 750, 720 and 700 $cm^{-1}$ and NMR peaks ($\delta_{TMS}^{CDCL_3}$) at 7.27 (phenyl; singlet; 5H), 5.8–5.1 (vinyl and C-9H; multiplet; 5H9, 4.30–3.75 (C$\underline{H}$OH; multiplet; 1H) and 1.40 ppm (15-C$\underline{H}_3$; singlet; 3H) and mass spectrum paks at M+ 528.3112 (calc'd. for $C_{90}H_{48}Si_2O_4$: 528.3091; as well as m/e 513, 438, 423, 333, 91.

EXAMPLE 30

(15S)-2,2-Difluoro-15-methyl-$PGF_{2\alpha}$, 1,9-lactone

A solution of (15S)-2,2-difluoro-15-methyl-$PGF_{2\alpha}$ methyl ester (150 mg) in 5 ml of methanol at 0° was treated with 4 ml of 3N aqueous potassium hydroxide and stirred under nitrogen at 0° for 30 min. The reaction mixture was acidified with cold aqueous potassium bisulfate and extracted thoroughly with ethyl acetate. The extract was washed with brine, dried over sodium sulfate and concentrated to afford a residue of (15S) 2,2-difluoro-15-methyl $PGF_{2\alpha}$.

The residue was immediately dissolved in 10 ml of anhydrous oxygen-free benzene, treated with triphenylphosphine (141 mg) and 2,2'-dpyridyl disulfide (118 mg), and stirred at room temperature for 20 min when TLC (AIX) analysis indicated that, in addition to the pyridinethiol ester formation, lactonization had already occurred as well. The solvent was removed under vacuum to yield a residue containing (15S) 2,2-difluoro-15-methyl·PGF$_{2\alpha}$ 1,9-lactone.

The residue was purified by chromatography on 60 g of neutral silica packed with 30% acetone/methylene chloride and eluted with 40% acetone/methylene chloride (approx. 6 ml fractions).

Those fractions which were homogeneous by TLC analysis (fractions 49–56) were combined to afford pure (15S) 2,2-difluoro-15-methyl-PGF$_{2\alpha}$, 1,9-lactone with NMR peaks ($\delta_{TMS}{}^{CDCl_3}$) at 5.90–5.10 (vinyl and C-9H; multiplet; 5H), 4.10–3.65 (CHOH; multiplet; 1H) and 1.26 ppm (CH$_3$; singlet; 3H).

The mass spectrum established molecular weight as m/e 530.3078 for the trimethylsilyl ether (calc'd. for C$_{27}$H$_{48}$Si$_2$O$_4$F$_2$: 530.3059).

EXAMPLE 31

PGD$_2$ 1,9-Lactone

A. A solution of PGF$_{2\alpha}$ 15-tetrahydropyranyl ether (1.7 g), triphenylphosphine (1.52 g) and 2,2'-dipyridyl disulfide (1.28 g) in 10 ml of oxygen-free benzene was stirred at room temperature overnight. The solution was diluted with 1.0 liter of oxygen-free benzene and was refluxed under nitrogen for 23 hrs, cooled to room temperature and concentrated under vacuum to afford PGF$_{2\alpha}$ 1,9-lactone 15-tetrahydropyranyl ether as an oil.

The oil was purified by chromatography on a column of 450 g of silica gel, packed with 30% ethyl acetate/hexane and eluted with 80 23 ml fractions of 50% ethyl acetate/hexane and 70 23 ml fractions of 60% ethyl acetate/hexane.

Those fractions containing homogeneous product by TLC analysis (fractions 100–150) were combined to give purified PGF$_{2\alpha}$,19-lactone 15-tetrahydrpyranyl ether as a light yellow oil with an Rf of 0.26 in 50% ethyl acetate/hexane on TLC and with an infrared spectrum containing peaks at 3500, 2980, 2910, 1,9-lactone 1580, 1530, 1450, 1420, 1360, 1345, 1320, 1260, 1220, 1200, 1180, 1120, 1080, 1020, 990, 970, 940, 905, 870, and 815 cm$^{31\ 1}$.

B. A solution of 5.5 g of PGF$_{2\alpha}$ 1,9-lactone 15-tetrahydropyranyl ether in 100 ml of acetone was cooled to −30° C. Then 1.1 equivalents (3.6 ml) of Jones' reagent (J. Org. Chem. 21, 1547, 1956) was added and the solution was maintained at −30° C, for 1 hr. Isopropanol (6 ml) was added, the solution was stirred for 30 minutes at −30° C, was poured into 600 ml of ice water, and was extracted three times with 1:2 ether/hexane. The combined organic extract was washed three times with brine, dried over MgSO$_4$, and concentrated under vacuum to give a residue containing PGD$_2$ 1,9-lactone 15-tetrahydropyranyl ether.

The residue was purified by chromatography on a column of 375 g of Mallinckrodt CC-4 silica gel, packed with 10% ethyl acetate/hexane and eluted with 25% ethyl acetate/hexane, collecting 23 ml fractions. Those fractions homogeneous by TLC (fractions 43–64) were combined to give PGD$_2$ 1,9-lactone 15-tetrahydropyranyl ether as a colorless oil with Rf of 0.50 in 35% ethyl acetate/hexane containing 1% HOAc on TLC and infrared peaks at 2980, 2910, 1750, 1450, 1360, 1340, 1260, 1230, 1200, 1180, 1130, 1080, 1020, 990, and 870 cm$^{-1}$.

C. A solution of PGD$_2$, 1,9-lactone, 15-tetrahydropyranyl ether (0.5 g) in 25 ml of 1:3:6 THF/H$_2$O/HOAc was warmed to 40° C for 1 hr. poured into 100 ml of cold brine and extracted three times with 1:1 ethyl acetate/hexane. The combined extract was washed with brine, ice cold saturated NaHCO$_3$ solution, dried over Na$_2$SO$_4$, and concentrated to give a residue containing PGD$_2$ 1,9-lactone as an oil.

The oil was purified by chromatography on 20 g of Mallinckrodt CC-4 silica gel, packed with 20% ethyl acetate/hexane and eluted with 40% ethyl acetate/hexane, collecting 2 ml fractions. Those fractions which were homogeneous by TLC analysis (fractions 25–42) were combined to give pure PGD$_2$, 1,9-lactone exhibiting an Rf of 0.37 in 50% ethyl acetate/hexane on TLC, and infrared peaks at 3460, 3000, 2960, 2920, 2860, 1740, 1580, 1560, 1450, 1365, 1335, 1265, 1230, 1205, 1175, 1130, 1070, 1050, 1025, 970 and 945 cm$^{-1}$. The NMR spectrum revealed peaks ($\delta_{TMS}{}^{CDCl_3}$) at 5.40 (vinyl, C-9H; multiplet; 5H), 4.0 (C-15 H; multiplet; 1H), 0.90 ppm (C-20 methyl; multiplet; 3H). The mass spectrum of the trimethylsilyl derivative showed a peak at 406.2522 (Calc'd. for TMS-derivative C$_{23}$H$_{38}$SiO$_4$ = 406.2539) as well as at m/e 391 (M+ − CH$_3$); 388 (M+ − H$_2$O); 378 (M+ − CO); 373 (M+ − (H$_2$O + CH$_3$)) and 335 (M+ − C$_5$H$_{11}$).

EXAMPLE 32

13,41-Didehydro-8$\beta$,9$\beta$,11$\beta$,12$\alpha$ PGF$_{2\alpha}$ 1,9-lactone and 13,14-didehydro PGF$_{2\alpha}$ 1,9-lactone Following the procedure of example 27 but substituting 13,14-didehydro-8$\beta$,9$\beta$,11$\beta$,12$\alpha$-PGF$_{2\alpha}$ [also known as ent-13-dehydro-15-epiprostaglandin F$_{2\alpha}$ (compound 2 of J. Fried and C. H. Lin, J. Med. Chem. 16, 429 (1973)] and 13,14-didehydro PGF$_{2\alpha}$ for (15S) 15-methyl PGF$_{2\alpha}$ there are produced 13,14-didehydro-8$\beta$,9$\beta$,11$\beta$,12$\alpha$-PGF$_{2\alpha}$, 1,9-lactone and 13,14-didehydro PGF$_{2\alpha}$, 1,9-lactone, respectively.

EXAMPLE 33

13,14-Dihydro PGF$_{2\alpha}$ 1,9-lactone

Following the procedure of example 27 but substituting 13,14-dihydro PGF$_{2\alpha}$ for (15S) 15-methyl PGF$_{2\alpha}$ there is produced 13,14-dihydro PGF$_{2\alpha}$ 1,9-lactone which exhibited a multiplet centered at 5.3 ppm (2H) in the NMR spectrum.

EXAMPLE 34

11-Deoxy PGF$_{2\alpha}$ 1,9-lactone

Following the procedure of example 27 but substituting 11-deoxy PGF$_{2\alpha}$ for (15S) 15-methyl PGF$_{2\alpha}$ there is produced 11-deoxy PGF$_{2\alpha}$ 1,9-lactone

EXAMPLE 35

In like manner, but substituting:
17-phenyl-18,19,20-trinor PGF$_{2\alpha}$
17-phenyl-18,19,20-trinor PGF$_{1\alpha}$
16-phenoxy-17,18,19,20-tetranor PGF$_{2\alpha}$
16-m-trifluoromethylphenoxy-17,18,19,20-tetranor PGF$_{2\alpha}$
16-m-chlorophenoxy-17,18,19,20-tetranor PGF$_{2\alpha}$
16-p-fluorophenoxy-17,18,19,20-tetranor PGF$_{2\alpha}$
(16S) 16-methyl PGF$_{2\alpha}$
(16R) 16-methyl PGF$_{2\alpha}$
16-methylene PGF$_{2\alpha}$ 16,16-dimethyl-4,5-didehydro PGF$_{1\alpha}$
5-oxa-PGF$_{1\alpha}$
16,16-difluoro PGF$_{2\alpha}$, and the like
for (15S) 15-methyl PGF$_{2\alpha}$ in the procedure of example 27, there are produced:
  17-phenyl-18,19,20-trinor PGF$_{2\alpha}$ 1,9-lactone
  17-phenyl-18,19,20-trinor PGF$_{1\alpha}$, 1,9-lactone
  16-phenoxy-17,18,19,20-tetranor PGF$_{2\alpha}$ 1,9-lactone
  16-m-trifluoromethylphenoxy-17,18,19,20-tetranor PGF$_{2\alpha}$1,9-lactone
  16-m-chlorophenoxy-17,18,19,20-tetranor PGF$_{2\alpha}$ 1,9-lactone
  16-p-fluorophenoxy-17,18,19,20-tetranor PGF$_{2\alpha}$ 1,9 lactone
  (16S) 16-methyl PGF$_{2\alpha}$ 1,9 lactone
  (16R) 16-methyl PGF$_{2\alpha}$ 1,9 lactone
  16-methylene PGF$_{2\alpha}$ 1,9 lactone
  16,16-dimethyl-4,5-didehydro PGF$_{1\alpha}$1,9 lactone
  5-oxa-PGF$_{1\alpha}$ 1,9 lactone
  16,16-difluoro PGF$_{1\alpha}$ 1,9 lactone

EXAMPLE 36

PGF$_{2\alpha}$, 1,11-lactone

A. Via PGF$_{2\alpha}$ 9,15-diacetate

1. A solution of PGD$_2$ (0.5 g) in 8 ml of pyridine at 0° was treated with 2 ml of acetic anhydride and stirred under nitrogen for 1.5 hr at 0° and 1.5 hr at 25°. TLC (70% ethyl acetate/hexane with 1% acetic acid) indicated about 85% conversion to a single less polar material. The reaction mixture was poured into ice/water/sodium bisulfate/ethyl acetate and extracted thoroughly with ethyl acetate. The extract was washed with brine, dried over sodium sulfate and concentrated to residue containing PGD$_2$ 9,15-diacetate.

The residue was dissolved in 50 ml of methanol and treated at 0° with sodium borohydride (500 mg) added in 50 mg portions every 2 minutes. Aqueous sodium bisulfate (1M) was added until the mixture was acidic and the product was isolated by extraction with ethyl acetate. The extract was washed and evaporated to a residue.

The residue was purified by chromatography on 70 g of acid-washed silica packed with 30% ethyl acetate/hexane and eluted as follows:

| | |
|---|---|
| 400 ml of 30% ethyl acetate/hexane | Fractions 1 – 22 |
| 500 ml of 40% ethyl acetate/hexane | Fractions 23 – 47 |
| 500 ml of 55% ethyl acetate/hexane | Fractions 48 – 72 |
| 500 ml of 70% ethyl acetate/hexane | Fractions 73 – 99 |
| 500 ml of 85% ethyl acetate/hexane | Fractions 100 – 126 |

The fractions of homogenous product (as judged by TLC) first eluted (fractions 79-88) were combined to give pure PGF$_{2\alpha}$, 9,15-diacetate with infrared peaks at 3500, 2700, 1750, 1725, 1375, 1240, 1040, 1020, 970 cm$^{-1}$ and NMR peaks ($\delta_{TMS}^{CDCl_3}$) at 5.85 (OH; broad singlet which shifts downfield on cooling; 2H), 5.70–5.00 (vinyl and C$\underline{H}$OAc; multiplet; 6H), 4.20–3.75: C$\underline{H}$OH; multiplet; 1H) and 2.03 ppm (OCOCH$_3$ singlet; 6H).

Saponification of 3 mg of this material in 0.5 ml of methanol and 0.5 ml of 3N aqueous sodium hydroxide at 25° for 3 hr afforded after acidification and extraction pure PGF$_{2\alpha}$.

The fractions of homogeneous product (as judged by TLC) eluted later (fractions 93-100) were combined to give pure 11-epi-PGF$_{2\alpha}$, 9,15-diacetate which, on saponification under the above conditions, afforded pure 11-epi PGF$_{2\alpha}$.

2. A solution of PGF$_{2\alpha}$, 9,15-diacetate 890 mg), triphenylphosphine (81 mg) and 2,2'-dipyridyl disulfide (68 mg) in 3 ml of dry, oxygen-free xylene was stirred at 25° under nitrogen for 5 hr, diluted with 100 ml of xylene, and heated at reflux for 18 hr. The solvent was removed in vacuo to yield a residue.

The residue was purified by chromatography on 15 g of neutral silica, packed and eluted (2 ml fractions) with 40% ether/hexane. Those fractions which were homogeneous (fractions 32-50) were combined and afforded pure PGF$_{3\alpha}$1,11-lactone, 9,15-diacetate with infrared peaks at 3500 (W, C=O overtone), 1750, 1450, 1370, 1240, 1140, 1100, 1050, 1020, 970 cm$^{-1}$.

3. A solution of PGF$_{2\alpha}$, 1,11-lactone, 9,15-diacetate (18 mg) and sodium bicarbonate (80 mg) in 2 ml of 1:1 methanol/water was stirred at 45° ± 5° for 55 hr. The reaction mixture was then diluted with brine and extracted with ethyl acetate. The extract was washed with brine, dried over sodium sulfate and concentrated to a residue.

The residue was purified by chromatography on 10 g of neutral silica packed with 1:1 ethyl acetate/hexane and eluted (1.5 ml fractions) with pure ethyl acetate.

Fraction 10 contained appreciable material but was only about 90% pure by tlc and was discarded. Fractions 11-17 were combined and afforded 8 mg of pure PGF$_{2\alpha}$, 1,11-lactone with an infrared spectrum with peaks at 3400, 3000, 2920, 2850, 1730, 1710, 1450, 1355, 1335, 1270, 1225, 1185, 1145, 1100, 1085, 1005, 965 and 705 cm$^{-1}$. Mobilities on TLC were:

Rf (20 acetone/80 methylene chloride/1.5 acetic acid) 0.24
Rf (75 ethyl acetate/25 hexane/1.5 acetic acid) 0.31
Rf (AIX) 0.49

A small sample (0.5 mg) of PGF$_{2\alpha}$ 1,11-lactone was saponified in 0.2 ml of methanol and 0.3 ml of 3N aqueous sodium hydroxide. After two hours at room temperature, the reaction mixture was acidified with aqueous sodium bisulfate and extracted with ethyl acetate. The extract was examined in 5 TLC systems and found to contain only PGF$_{2\alpha}$.

B. Via PGF$_{2\alpha}$ 9,15-bis(triphenylsilyl ether)

1a. A solution of PGD$_2$ (1g) in 25 ml of anhydrous pyridine was stirred at 0° and treated with triphenylsilyl chloride (3 g) added in one portion. The resulting mixture was stirred for 6 hr at 25° under nitrogen, cooled to 0°, diluted with 100 ml of cold tetrahydrofuran and 40 ml of ice, water, and stirred an additional 45 min at 0°. The mixture was then poured into brine, acidified with 325 ml of 1N sodium bisulfate and extracted thoroughly with 1:1 ethyl acetate/hexane. The combined extract was washed with brine, dried over sodium sulfate and concentrated under vacuum to give a residue.

The residue was purified by chromatography on 300 g of acid-washed silica packed with 10% ethyl acetate/hexane and eluted with 700 ml of 10% ethyl acetate/hexane followed by 2000 ml of 20% ethyl acetate/hexane. Those fractions which were homogeneous on TLC (fractions 45-67) were combined to give pure PGD$_2$, 9,15-bis(triphenylsilyl ether) with infrared peaks at 3300, 3100, 2700, 1750, 1720, 1600, 1490, 1430, 1370, 1240, 1115, 1040, 1000, 970, 740, 710 and 700 cm$^{-1}$ and NMR peaks ($\delta_{TMS}^{CDCl_3}$) at 10.75 (CO$_2$H; broad singlet which shifts on cooling; 1H), 7.90–7.20 (phenyl; multiplet; 30H), 5.75-5.05 (vinyl; multiplet; 4H) and 4.75-4.15 ppm (C$\underline{H}$OSi; multiplet; 2H).

1b. Alternatively, a mixture of PGD$_2$ (200 mg) and triphenylsilyl chloride (600 mg) in 5 ml of anhydrous pyridine was stirred at 25° for 6 hr. The mixture was then cooled to 0° and poured into a rapidly stirred mixture of ether/ice/brine/H$_2$O/2N sodium bisulfate. After thorough extraction with ether, the organic layer was washed with brine and dried over sodium sulfate. The solvent was removed to yield the product as a residue. The residue was purified by chromatography on 130 g of acid silica. The column was eluted with 1000 ml of 10% ethyl acetate/hexane (fractions 1-70) followed by 1000 ml of 20% ethyl acetate/hexane (fractions 71-130).

Those fractions eluted early which were homogeneous by TLC after spotting on a plate pre-moistened with the developing solent were combined (fractions 32-44) to give PGD$_2$, 9,15-bis(triphenylsilyl ether), triphenylsilyl ester with an infrared spectrum with peaks at 3100, 3060, 1750, 1600, 1430, 1370, 1240, 1160, 1120, 1045, 1000, 970, 745, 712 and 700cm$^{-1}$ and NMR peaks ($\delta_{TMS}^{CDCl_3}$) at 8.0-7.1 (phenyl; multiplet; 45H), 5.80-5.10 (vinyl; multiplet; 4H), 4.75-4.14 (C$\underline{H}$OSi; multiplet; 2H).

Those later fractions homogeneous by TLC (fractions 83-97) were combined to give pure PGD$_2$ 9,15-bis(triphenylsilyl ether) identical by IR and NMR to that prepared by the above procedure (1a).

1c. To a solution of PGD$_2$ 9,15-bis(triphenylsilyl ether) triphenylsilyl ester (2.33 g) in 200 ml of tetrahydrofuran at 0° was added 50 ml of water in one portion with stirring, followed by the dropwise solution of 25 ml of water containing 200 mg of pyridine hydrochloride. After 2.5 hr at 0°, the mixture was diluted with brine and extracted with 1:1 ethyl acetate/hexane. The extract was washed with cold aqueous sodium bisulfate and brine, dried over sodium sulfate and concentrated to a residue.

The residue was purified by chromatography on 300 g of silica packed with 10% ethyl acetate/hexane and eluted with 700 ml of the same solvent and 200 ml of 20% ethyl acetate/hexane. Those fractions homogeneous by TLC (fractions 41-68) were combined to yield pure PGD$_2$ 9,15-bis(triphenylsilyl ether), identical by IR and NMR to the product of the above procedure (1a).

2. To a solution of PGD$_2$ 9,15-bis(triphenylsilyl ether) 4.10 g) in 250 ml of methanol at 0° was added with stirring sodium borohydride (3 g) in 100 mg portions over 15 min. After an additional 15 min at 0° the reaction mixture was carefully poured into a rapidly stirred mixture of ice/water/dilute sodium bisulfate/1:1 ethyl acetate: hexane. After separation of the two phases, the aqueous layer was extracted twice more with 1:1 ethyl acetate:hexane. The combined organic layer was washed with brine, dried over sodium sulfate and concentrated in vacuo to give a residue.

The residue was purified by chromatography on 450 g of acid washed silica packed with 10% ethyl acetate/hexane and eluted with 20% ethyl acetate/hexane. The first 800 ml of eluate was discarded; then 19 ml fractions were collected. Those fractions homogenous by TLC (fractions 40-75) were combined to give PGF$_{2\alpha}$, 9,15-bis(triphenylsilyl ether).

To confirm the identity of the above material, a 2 mg portion was stirred for 2 hr at 45° in a mixture of 6 drops of tetrahydrofuran, 3 drops of water and 1 drop of 85% phosphoric acid. The mixture was then diluted with brine and extracted with ethyl acetate. TLC analysis of the extracts on boric acid impregnated plates showed only PGF$_{2\alpha}$ and none of the 11$\beta$-epimer, thus confirming the assignment stereochemistry at C$_{11}$ for the borohydride reduction product.

3. A solution of PGF$_{2\alpha}$, 9,15-bis(triphenylsilyl ether) (2.90 g) 2,2'-dipyridyl disulfide (1.10 g) and triphenylphosphine (1.31 g) in 40 ml of dry, oxygen-free xylene was stirred at 25° under nitrogen for 10 hr. The mixture was then diluted with 800 ml of xylene and heated at reflux for 24 hr. The xylene was removed in vacuo at 30°-35° to yield a dark red residue.

The residue was purified by chromatography on 450 g of neutral silica packed and eluted with benzene. After discarding the first 200 ml of eluate, 50 ml fractions were collected. Those fractions homogeneous by TLC (fractions 30-48) were combined to give pure PGF$_{2\alpha}$, 1,11-lactone, 9,15-bis(triphenylsilyl ether) with infrared bands at 3100, 3050, 1730, 1590, 1480, 1440, 1420, 1325, 1260, 1220, 1180, 1140, 1110, 1000, 970, 905, 900, 875, 740, 710 and 700 cm$^{-1}$.

4. A mixture of PGF$_{2\alpha}$, 1,11-lactone, 9,15-bis(triphenylsilyl ether) (2.20 g), 100 ml of tetrahydrofuran, 80 ml of water and 20 ml of 85% phosphoric acid was stirred and heated at 45° for 2 hours. The reaction mixture was concentrated in vacuo to about one half of the original volume, water was added and the product was isolated by extraction with 3:1 ethyl acetate/hexane. The combined extract was washed with aqueous sodium bicarbonate and brine, dried over magnesium sulfate and then evaporated to give a residue.

The residue was purified by chromatography on 125 g of neutral silica packed with 25% ethyl acetate/hexane and eluted (14 ml fractions) as follows:

800 ml 40% ethyl acetate/hexane (single fraction)
800 ml 55% ethyl acetate/hexane
1000 ml 70% ethyl acetate/hexane Those fractions homogeneous by tlc were combined to yield pure PGF$_{2\alpha}$, 1,11-lactone with an infrared spectrum identical to that of the product produced by the procedure of example 36A.

EXAMPLE 37

TLC Behavior of PGF$_{2\alpha}$, 1,9-Lactone, PGF$_{2\alpha}$, 1,11-Lactone and PGF$_{2\alpha}$, 1,15-Lactone In order to compare meaningfully the TLC mobility of the three possible lactones of PGF$_{2\alpha}$, these were run on the same plates in several solvent systems. Each plate (2 × 3") was developed twice successively in the same solvent prior to visualization.

| Solvent | Compound | Rf |
|---|---|---|
| 20 acetone/ 80 methylene chloride | PGF$_2\alpha$ 1,9-lactone | 0.25 |
| | PGF$_2\alpha$ 1,11-lactone | 0.54 |
| | PGF$_2\alpha$ 1,15-lactone | 0.45 |
| 70 ethyl acetate/ 30 hexane | PGF$_2\alpha$, 1,9-lactone | 0.23 |
| | PGF$_2\alpha$, 1,11-lactone | 0.52 |
| | PGF$_2\alpha$, 1,15-lactone | 0.48 |

For purposes of comparison, the most polar of the lactones—PGF$_{2\alpha}$, 1,9-lactone (U-48,687) — has about the same TLC mobility as PGE$_2$ methyl ester.

EXAMPLE 38

PGF$_{1\alpha}$1,11-lactone

Following the procedures of examples 36A and B but substituting PGD$_1$ for PGD$_2$ there is produced PGF$_{1\alpha}$ 1,11-lactone.

EXAMPLE 39

(15S) 15-methyl PGF$_{2\alpha}$ 1,11-lactone

Following the procedure of examples 36 but substituting (15S) 15-methyl PGD$_2$ (U.S. Pat. No. 3,878,239) for PGD$_2$ there is produced (15S) 15-methyl PGF$_{2\alpha}$ 1,11-lactone.

In like manner, substituting (15R) 15-methyl PGD$_2$, (16S) 16-methyl PGD$_2$, and (16R) 16-methyl PGD$_2$ for PGD$_2$ in the procedure of example 36 there are produced (15R) 15-methyl PGF$_{2\alpha}$ 1,11-lactone, (16S) 16-methyl PGF$_{2\alpha}$ 1,11-lactone and (16R) 16-methyl PGF$_{2\alpha}$ 1,11-lactone, respectively.

EXAMPLE 40

PGE$_2$ 1,11-Lactone

A solution of PGF$_{2\alpha}$ 1,11-lactone in acetone is converted to the corresponding 15-monotrimethylsilyl ether by the method of example 3. Following purification by chromatography the PGF$_{2\alpha}$ 1,11-lactone 15-trimethylsilyl ether is oxidized with Collins' reagent by the procedure of example 3 to produce PGE$_2$ 1,11-lactone 15-trimethylsilyl ether. The crude material is purified by chromatography and hydrolyzed in dilute citric acid by the method of example 3 to produce crude PGE$_2$ 1,11-lactone. Careful chromatography or crystallization affords PGE$_2$ 1,11-lactone in essentially pure form.

EXAMPLE 41

PGE$_1$ 1,11-Lactone

In like manner, substituting PGF$_{1\alpha}$ 1,11-lactone in the procedure of example 39 there is produced PGE$_1$ 1,11-lactone.

Similarly, substituting (15S) 15-methyl PGF$_{2\alpha}$ 1,11-lactone, (15R) 15-methyl PGF$_{2\alpha}$ 1,11-lactone, (16s) 16-methyl PGF$_{2\alpha}$, 1,11-lactone, and (16R) 16-methyl PGF$_{2\alpha}$, 1,11-lactone for PGF$_{2\alpha}$1,11-lactone, there are produced (15S) 15-methyl PGE$_2$ 1,11-lactone, (15R) 15-methyl PGE$_2$, 1,11-lactone, (16S) 16-methyl PGE$_2$ 1,11-lactone, and (16R) 16-methy-PGE$_2$ 1,11-lactone, respectively.

EXAMPLE 42

13,14-Didehydro-8$\beta$,9$\beta$,11$\beta$,12$\alpha$PGF$_{1\alpha}$1,11-lactone A solution of 13,14-didehydro-8$\beta$,9$\beta$,11$\beta$,12$\alpha$-PGF$_{2\alpha}$ [also known as ent-13-dehydro-15-epiprostaglandin PGF$_{2\alpha}$(compound 2, J. Fried and C. H. Lin J. Med. Chem. 16 429 (1973)] is converted to a mixture of 11,15-bis(trimethylsilyl ether) and the corresponding trimethylsilyl ester as described by Fried and Lin for the methyl ester of their compound 2 (ibid). The silyl mixture is treated directly with acetic anhydride and pyridine for 3 hours at room temperature followed by water to produce the 9-acetate and then with dilastic acid, to remove the silyl protecting groups, and the resulting crude 13,14-didehydro-8$\beta$,9$\beta$,11$\beta$,12$\alpha$ PGF$_{2\alpha}$9$\beta$-monoacetate is extracted into ether. The extract is washed, dried, and evaporated to a residue. The residue is purified by chromatography over neutral silica combining those fractions essentially homogeneous by TLC analysis.

The thus obtained purified 9-monoacetate is treated at 0° for 15 min with t-butyldimethylsilyl chloride and imidazole in DMF to produce a mixture containing the corresponding 9$\beta$-monoacetate 15-mono-t-butyldimethylsilyl ether) which, after repeated chromatographic purifications, is substituted for PGF$_{2\alpha}$9,15-diacetate in the procedure of example 36A-2 to produce crude 13,14-didehydro-8$\beta$,9$\beta$,11$\beta$,12$\alpha$-PGF$_{2\alpha}$1,11-lactone 9-acetate 15-t-butyldimethylsilyl ether. The crude product thus produced is treated sequentially without purification by the procedures of example 24-C to remove the 15-silyl group and of example 36A-3 to remove selectively the 9-acetate. The thus produced crude product is purified by repeated chromatography over neutral silica to afford essentially pure 13,14-didehydro-8$\beta$,9$\beta$,11$\beta$,12$\alpha$-PGF$_{2\alpha}$1,11-lactone.

EXAMPLE 43

13,14-Dihydro PGF$_{2\alpha}$1,11-lactone 13,14-Dihydro PGF$_{2\alpha}$1,9-lactone (produced by the procedure of example 33) is treated with triphenylsilyl chloride by the procedure of example 36B-1b to produce the 11,15-bis(triphenylsilyl ether). The bis ether is saponified with aqueous-methanolic sodium hydroxide to produce 13,14-dihydro PGF$_{2\alpha}$11,15-bis(trimethylsilyl ether) which is acetylated with acetic anhydride in pyridine for 3 hours at room temperature followed by water to produce 13,14-dihydro-PGF$_{2\alpha}$9-acetate 11,15-bis(trimethylphenyl ether). The thus produced product is purified by chromatography over silica and is then treated by the procedure of example 36B-4 to remove the silyl groups, affording, after purification by chromatography, essentially pure 13,14-dihydro PGF$_{2\alpha}$9-acetate.

The thus produced mono acetate is selectively silylated by treatment with t-butyldimethylsilyl chloride and imidazole at 0° in DMF for 20 minutes to produce a mixture containing 13,14-dihydro PGF$_{2\alpha}$9-acetate 15-t-butyldimethylsilyl ether. After repeated chromatographic purification, the thus obtained material is treated by the procedure of 36B-3to yield, after chromatographic purification 13,14-dihydro-PGF$_{2\alpha}$1,11-lactone 9-acetate, 15-t-butyldimethylsilyl ether. The protecting groups are selectively removed without intermediate purification by the methods of example 24-C and 36A-3. Chromatographic purification of the thus produced product affords 13,14-dihydro PGF$_{2\alpha}$1,11-lactone in essentially pure form.

I claim:

1. A pharmaceutical composition comprising an effective amount of a lactone which is the 1,11-lactone or the 1,15-lactone of prostaglandin or prostaglandin analog in combination with a pharamceutical carrier formulated to deliver said prostaglandin or prostaglandin analog to an esterase-containing tissue area of a mammal.

2. A composition according to claim 1 wherein the lactone is the 1,15-lactone.

3. A composition according to claim 2 formulated for use in a human.

4. A composition according to claim 2 formulated for use in a domestic animal.

5. A composition according to claim 3 formulated for subcutaneous or intramuscular use.

6. A composition according to claim 3 formulated for intravaginal use.

7. A composition according to claim 4 formulated for subcutaneous or intramuscular use.

8. A composition according to claim 2 wherein the prostaglandin or prostaglandin analog is of the $PGF_{2\alpha}$-type.

9. A composition according to claim 2 wherein the prostaglandin is $PGF_{2\alpha}$.

10. A composition according to claim 2 wherein the prostaglandin analog is 15(S)-15-methyl-$PGF_{2\alpha}$.

11. A composition according to claim 2 wherein the prostaglandin analog is 13,14-didehydro-$8\beta,9\beta,11\beta,12\alpha$-$PGF_{2\alpha}$.

12. A compositon according to claim 2 wherein the prostaglandin analog is 13,14-dihydro-$PGF_{2\alpha}$.

13. A composition according to claim 2 wherein the prostaglandin analog is of the 11-deoxy-$PGF_{60}$-type.

14. A composition according to claim 2 wherein the prostaglandin analog is of the PGD-type.

15. A composition according to claim 2 wherein the prostaglandin or prostaglandin analog is of the $PGE_1$-type.

16. A composition according to claim 2 wherein the prostaglandin is $PGE_1$.

17. A composition according to claim 2 wherein the prostaglandin or prostaglandin analog is of the $PGE_2$-type.

18. A composition according to claim 2 wherein the prostaglandin is $PGE_2$.

19. A composition according to claim 2 wherein the prostaglandin analog is 16,16-dimethyl-$PGE_2$.

20. A composition according to claim 2 wherein the prostaglandin or prostaglandin analog is of the PGA-type.

21. A composition according to claim 2 wherein the prostaglandin analog is of the 11-deoxy-PGE-type.

22. A composition according to claim 1 wherein the lactone is the 1,11-lactone.

23. A composition according to claim 22 formulated for use in a human.

24. A composition according to claim 22 formulated for use in a domestic animal.

25. A composition according to claim 23 formulated for subcutaneous or intramuscular use.

26. A composition according to claim 23 formulated for intravaginal use.

27. A composition according to claim 24 formulated for subcutaneous or intramuscular use.

28. A composition according to claim 22 wherein the prostaglandin or prostaglandin analog is of the $PGF_{2\alpha}$-type.

29. A composition according to claim 22 wherein the prostaglandin is $PGF_{2\alpha}$.

30. A composition according to claim 22 wherein the prostaglandin analog is 15(S)-15-methyl-$PGF_{2\alpha}$.

31. A composition according to claim 22 wherein the prostaglandin analog is 13,14-didehydro-$8\beta,9\beta,11\beta,12\alpha$-$PGF_{2\alpha}$.

32. A composition according to claim 22 wherein the prostaglandin analog is 13,14-dihydro-$PGF_{2\alpha}$.

33. A composition according to claim 22 wherein the prostaglandin or prostaglandin analog is of the $PGE_1$-type.

34. A composition according to claim 22 wherein the prostaglandin is $PGE_1$.

35. A composition according to claim 22 wherein the prostaglandin or prostaglandin analog is of the $PGE_2$-type.

36. A composition according to claim 22 wherein the prostaglandin is $PGE_2$.

37. A composition according to claim 22 wherein the prostaglandin analog is 16,16-dimethyl-$PGE_2$.

38. An improved method of administering an effective amount of a prostaglandin or a prostaglandin analog to esterase-containing tissues of a mammal which comprises administering to said mammal a lactone which is the 1,11-lactone or the 1,15-lactone of said prostaglandin or prostaglandin analog in combination with a pharmaceutical carrier.

* * * * *

UNITED STATES PATENT OFFICE
CERTIFICATE OF CORRECTION

Patent No. 4,067,991    Dated 10 January 1978

Inventor(s) Gordon L. Bundy

It is certified that error appears in the above-identified patent and that said Letters Patent are hereby corrected as shown below:

Column 1, lines 28-34, should appear as follows instead of as appears in the patent:

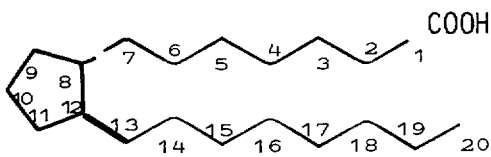

Column 3, line 62, "recogniaed" should read -- recognized --;
Column 5, line 49, "as position 1" should read -- at position 1 --; line 59, "PGF₆ₒ-type" should read -- PGFα-type --;
Column 9, line 21, "natrual" should read -- natural -- line 64, "c-15" should read -- C-15 --; line 65, "lctone function" should read -- lactone function --;
Column 10, line 10, "towrd" should read -- toward --;
Col. 12, line 7, "PGF₂₌" should read -- PGF₂α --; line 50, "1654, 163." should read -- 164, 163. --;
Column 14, line 51, "50M, 426," should read -- 501, 426, --;
Column 15, line 14, "1H9," should read -- 1H), --; line 66, "13,14dehydro-" should read -- 13,14-didehydro- --;
Column 17, line 34, "ethyl acette" should read -- ethyl acetate -- lines 47-48, "and PGE₁ 1,15 lactone and PGE₁ 1,15 lactone" should read -- and PGE₁ 1,15 lactone --; line 63, "wate," should read -- water, --;
Column 18, line 6, "cm³¹ ¹" should read -- cm⁻¹ --; line 12, "PGF₂60," should read -- PGF₂α, --; line 54, "PGF₂α, 1,1,5-lactone," should read -- PGF₂α, 1,15-lactone, --; line 59, "5.75-5.0" should read -- 5.75-5.50 --;
Col. 20, line 38, "M⁺ Apparent" should read -- M+ Apparent --; line 51, "idendentical" should read -- identical --;
Column 21, line 13, "cm³¹ ¹" should read -- cm⁻¹ --; line 46, "2H9," should read -- 2H), --; line 53, "4.28" should read -- 5.28 --; line 56, "ent riplet," should read -- ent triplet, --; line 68, "PGFα 1,9 lactone"

UNITED STATES PATENT OFFICE
CERTIFICATE OF CORRECTION

Patent No. 4,067,991  Dated 10 January 1978

Inventor(s) Gordon L. Bundy

It is certified that error appears in the above-identified patent and that said Letters Patent are hereby corrected as shown below:

should read -- $PGF_2\alpha$ 1,9 lactone --;
   Column 22, line 47, "1265, 12225," should read -- 1265, 1225, --; line 50, "5H9," should read -- 5H), --; line 52, "$C_{90}H_{48}Si_2O_4$:" should read -- $C_{30}H_{48}Si_2O_4$: --; line 68, "2,2'-dpyridyl" should read -- 2,2'-dipyridyl --;
   Column 23, line 39, "$PGF_2\alpha$, 19-lactone" should read -- $PGF_2\alpha$ 1,9-lactone --; lines 42-43, "2910, 1,9-lactone 1580," should read -- 2910, 1750, 158+, --;
   Column 24, line 29, "13,41-Didehydro-" should read -- 13,14-Didehydro- --
   Column 26, line 3, "890 mg)," should read -- (90 mg), --; line 13, "$PGF_3\alpha$" should read -- $PGF_2\alpha$ --;
   Column 27, line 24, "4.75-4.14" should read -- 4.75-4.15 --;
   Column 31, line 20, "$PGF_{60}$-type" should read -- $PGF\alpha$-type --.

Signed and Sealed this

Twenty-eighth Day of July 1981

[SEAL]

Attest:

GERALD J. MOSSINGHOFF

Attesting Officer     Commissioner of Patents and Trademarks